US012624340B2

(12) United States Patent
Cho et al.

(10) Patent No.:  US 12,624,340 B2
(45) Date of Patent:  May 12, 2026

(54) COMPOSITION FOR CULTURING BRAIN ORGANOID BASED ON DECELLULARIZED BRAIN MATRIX AND METHOD FOR PREPARING SAME

(71) Applicant: INDUSTRY-ACADEMIC COOPERATION FOUNDATION, YONSEI UNIVERSITY, Seoul (KR)

(72) Inventors: Seung Woo Cho, Seoul (KR); Ann Na Cho, Seoul (KR); Jung Seung Lee, Seoul (KR); Yoonhee Jin, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 18/347,142

(22) Filed: Jul. 5, 2023

(65) Prior Publication Data

US 2023/0374449 A1     Nov. 23, 2023

Related U.S. Application Data

(62) Division of application No. 16/448,954, filed on Jun. 21, 2019, now abandoned.

(30) Foreign Application Priority Data

Jun. 21, 2018    (KR) ........................ 10-2018-0071562

(51) Int. Cl.
| | |
|---|---|
| *C12M 1/12* | (2006.01) |
| *C12N 5/00* | (2006.01) |
| *C12N 5/0793* | (2010.01) |

(52) U.S. Cl.
CPC ........... *C12N 5/0619* (2013.01); *C12M 25/14* (2013.01); *C12N 5/0062* (2013.01); *C12N 5/0068* (2013.01); *C12N 2513/00* (2013.01); *C12N 2533/90* (2013.01)

(58) Field of Classification Search
None
See application file for complete search history.

(56) References Cited

U.S. PATENT DOCUMENTS

| | | |
|---|---|---|
| 2014/0178450 A1 | 6/2014 | Christman et al. |
| 2015/0037434 A1 | 2/2015 | Freytes et al. |
| 2016/0051731 A1 | 2/2016 | Matsuda et al. |
| 2018/0353648 A1 | 12/2018 | Jung et al. |

FOREIGN PATENT DOCUMENTS

| | | |
|---|---|---|
| KR | 2018-0025817 A | 3/2018 |
| WO | 2017/060884 A1 | 4/2017 |
| WO | 2018/013612 A1 | 1/2018 |

OTHER PUBLICATIONS

Crapo et al., Biomaterials 33 (2012) 3539-3547 (Year: 2012).*
Garreta et al., Materials Today, vol. 20, No. 4, May 2017 (Year: 2017).*

(Continued)

*Primary Examiner* — Evelyn Y Pyla
(74) *Attorney, Agent, or Firm* — NKL Law; Jae Youn Kim

(57) ABSTRACT

Provided is a method for preparing a composition for culturing a brain organoid, the method comprising (a) decellularizing brain tissue; (b) drying the brain tissue; and (c) gelating the brain tissue.

1 Claim, 26 Drawing Sheets

(56) References Cited

OTHER PUBLICATIONS

Koh et al., Scientific Reports, (2018) 8:4608, pp. 1-12 (Year: 2018).*

Choi Nature, vol. 515, Nov. 13, 2014, pp. 274-292 (Year: 2014).*

Gilbert et al., Journal of Surgical Research 152, 135-139 (2009) (Year: 2009).*

Lancaster et al., Nat biotechnol. Jul. 2017; 35(7): 659-666, published online May 31, 2017 (Year: 2017).*

Tao et al., Cell Stem Cell 19, Nov. 3, 2016 (Year: 2016).*

Medberry, Christopher J. et al., "Hydrogels derived from central nervous system extracellular matrix", Biomaterials., Jan. 1, 2013 (Jan. 1, 2013), pp. 1033-1040, vol. 34, No. 4.

Laurent, Jeremie et al., "Convergence of microengineering and cellular self-organization towards functional tissue manufacturing", Nature Biomedical Engineering, Dec. 12, 2017 (Dec. 12, 2017), pp. 939-956, vol. 1, No. 12.

Nguyen, Eric H. et al., "Versatile synthetic alternatives to Matrigel for vascular toxicity screening and stem cell expansion", Nature Biomedical Engineering, Jul. 1, 2017 (Jul. 1, 2017), vol. 1, No. 7.

Soofi, Shauheen S. et al., "The elastic modulus of Matrigel0̂(TM) as determined by atomic force microscopy", Journal of Structural Biology, Sep. 1, 2009 (Sep. 1, 2009), pp. 216-219, vol. 167, No. 3.

Jin, Yoonhee et al., "Three-dimensional brain-like microenvironments facilitate the direct reprogramming of fibroblasts into therapeutic neurons", Nature Biomedical Engineering, Jul. 11, 2018 (Jul. 11, 2018), pp. 522-539, vol. 2, No. 7.

Disha Sood et al., "Fetal Brain Extracellular Matrix Boosts Neuronal Network Formation in 3D Bioengineered Model of Cortical Brain Tissue", ACS Biomaterials Science & Engineering, 2016, pp. 131-140.

Madeline A Lancaster et al., "Generation of cerbral organoids from human pluripotent stem cells", Sep. 4, 2014, Nature Protocols, vol. 9 No. 10, pp. 2329-2340.

Jessica A. DeQusach et al., "Decellularized Porcine Brain Matrix for Cell Culture and Tissue Engieering Scaffolds", Oct. 11, 2011, vol. 17, Nos. 21 and 22, 2011, pp. 2583-2592.

* cited by examiner

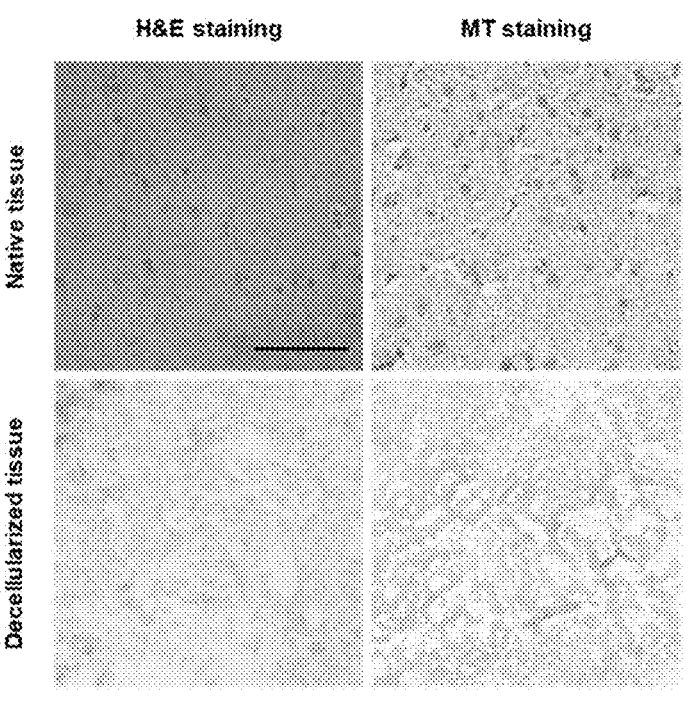
FIG. 2A
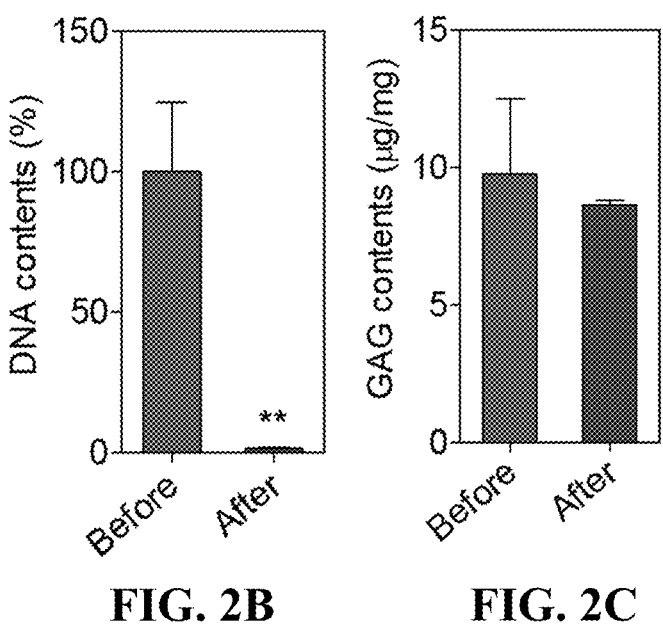
FIG. 2B          FIG. 2C

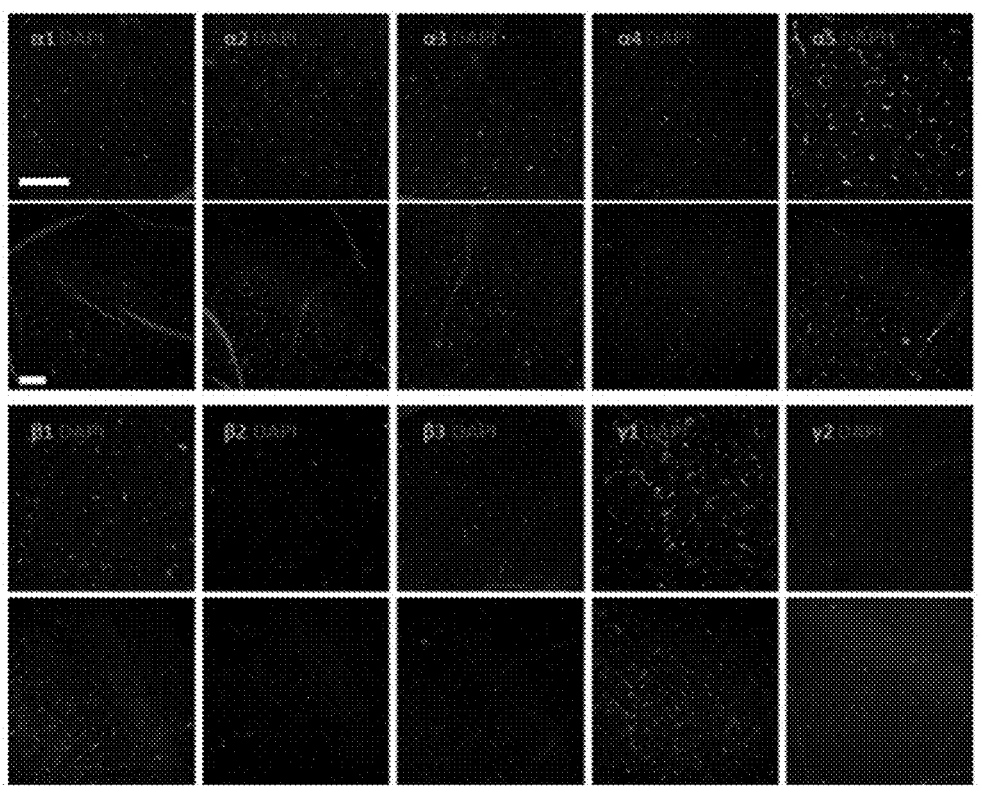

FIG. 3A

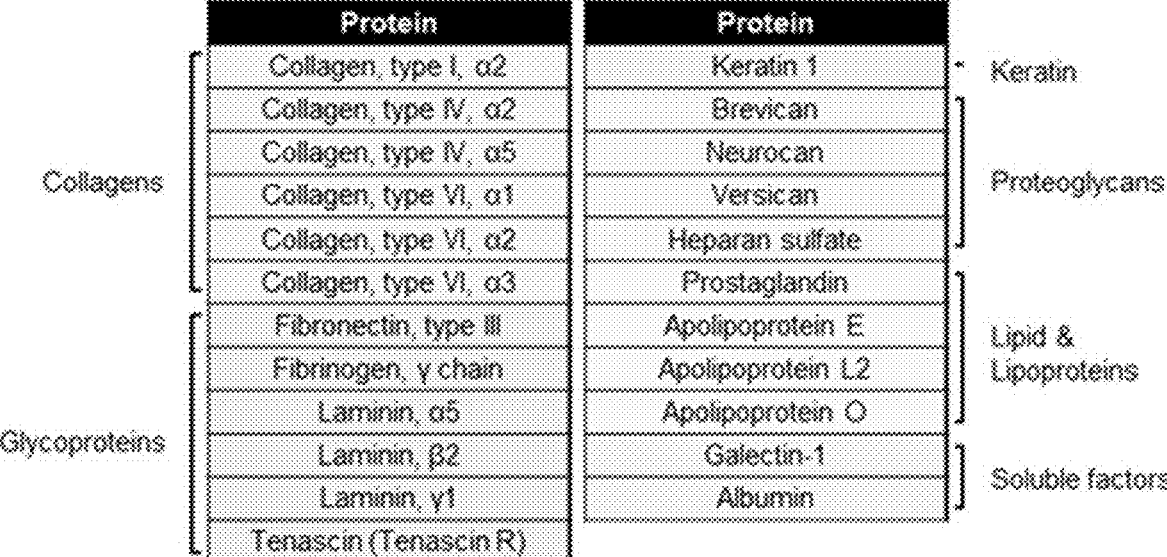

| Protein | Protein | |
|---|---|---|
| Collagen, type I, α2 | Keratin 1 | Keratin |
| Collagen, type IV, α2 | Brevican | |
| Collagen, type IV, α5 | Neurocan | |
| Collagen, type VI, α1 | Versican | Proteoglycans |
| Collagen, type VI, α2 | Heparan sulfate | |
| Collagen, type VI, α3 | Prostaglandin | |
| Fibronectin, type III | Apolipoprotein E | Lipid & |
| Fibrinogen, γ chain | Apolipoprotein L2 | Lipoproteins |
| Laminin, α5 | Apolipoprotein O | |
| Laminin, β2 | Galectin-1 | |
| Laminin, γ1 | Albumin | Soluble factors |
| Tenascin (Tenascin R) | | |

Collagens — rows Collagen, type I, α2 through Collagen, type VI, α3

Glycoproteins — rows Fibronectin, type III through Tenascin (Tenascin R)

FIG. 3B

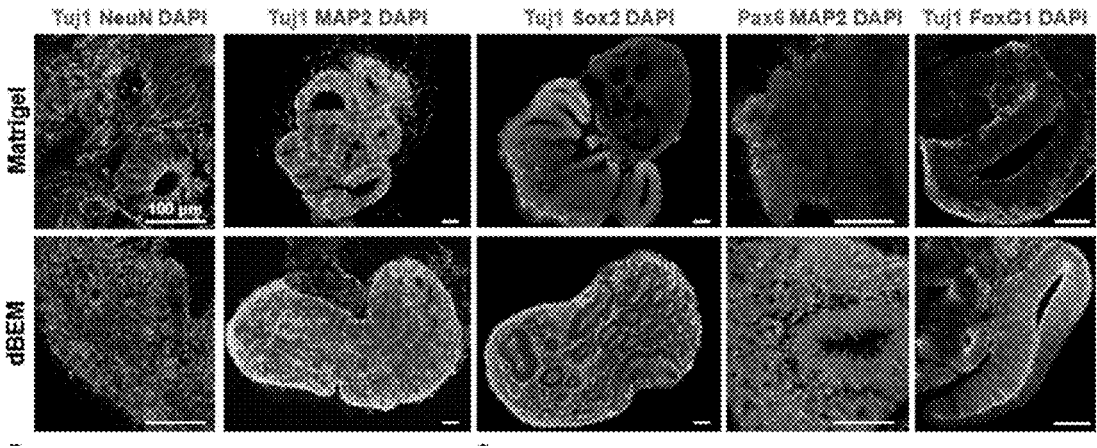
FIG. 7A
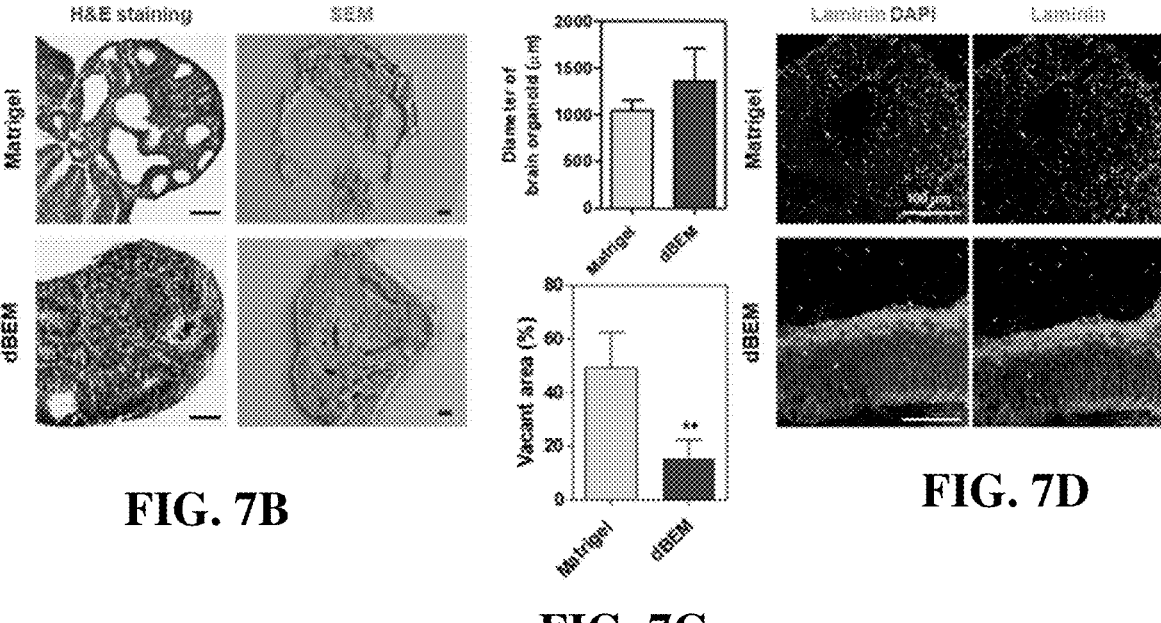
FIG. 7B
FIG. 7C
FIG. 7D

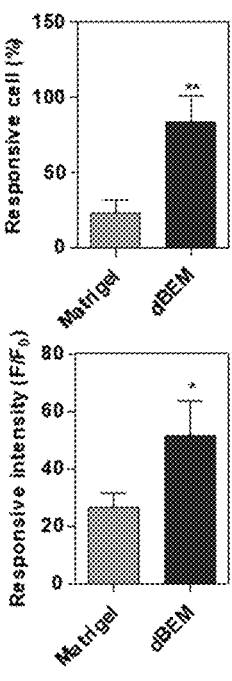
FIG. 10D
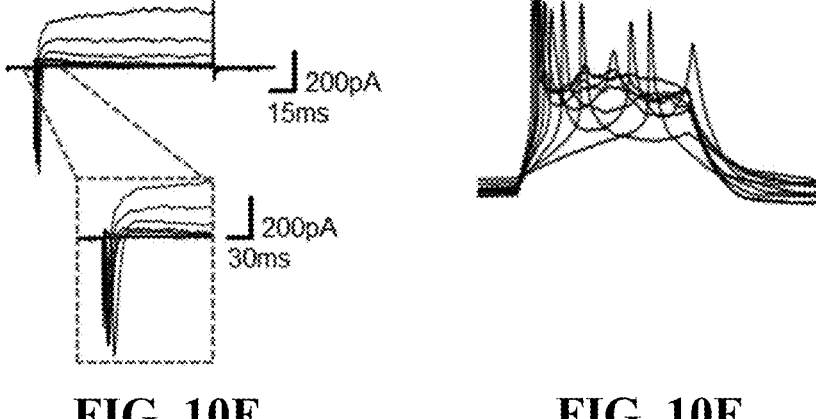
FIG. 10E FIG. 10F

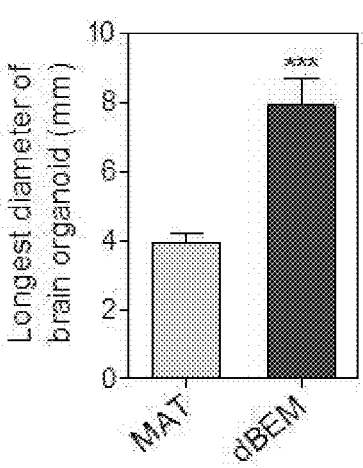
FIG. 12D
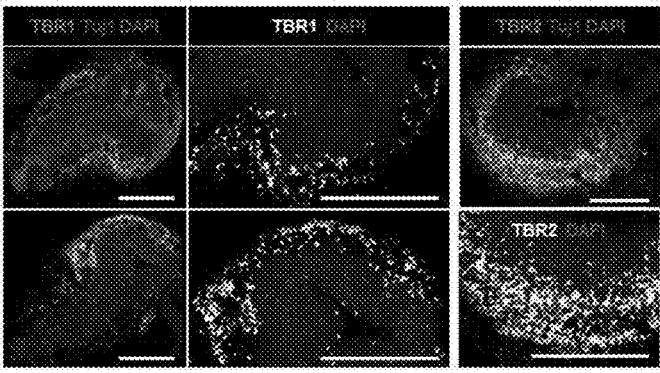
FIG. 12E
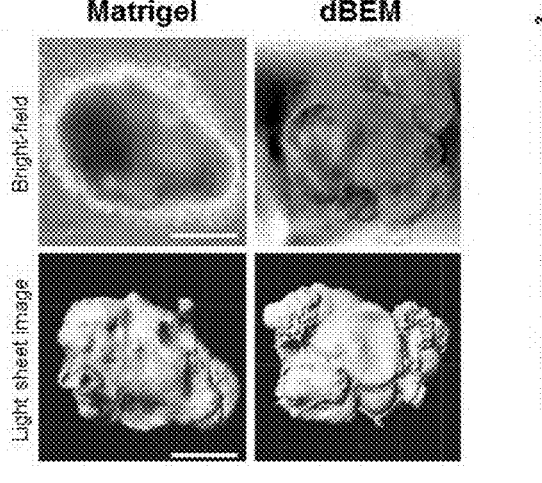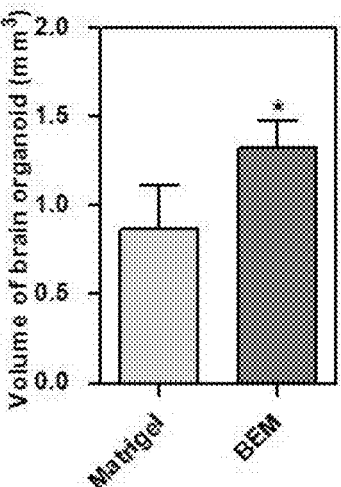
FIG. 12F FIG. 12G

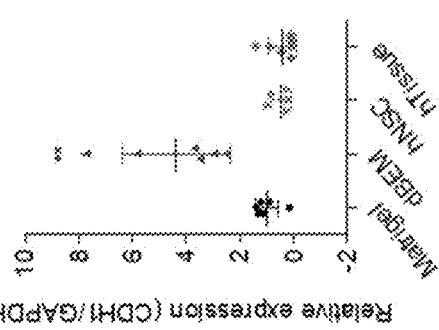
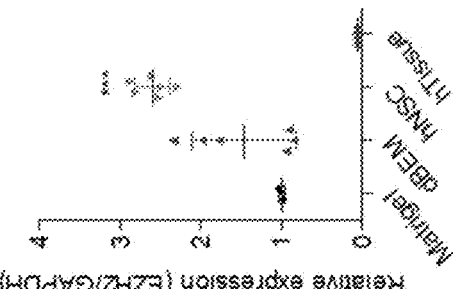
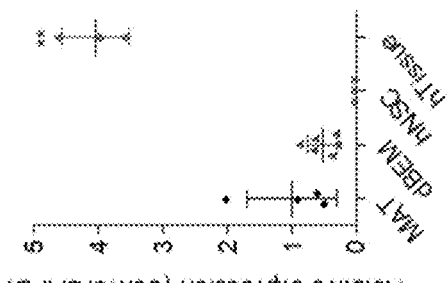
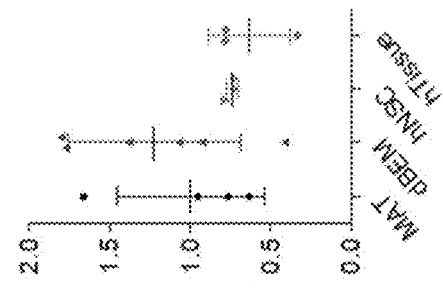
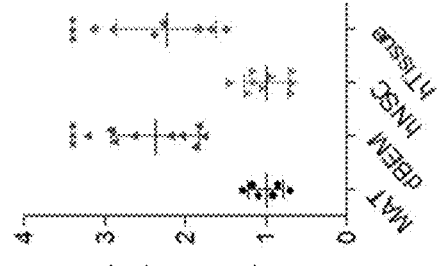
FIG. 14

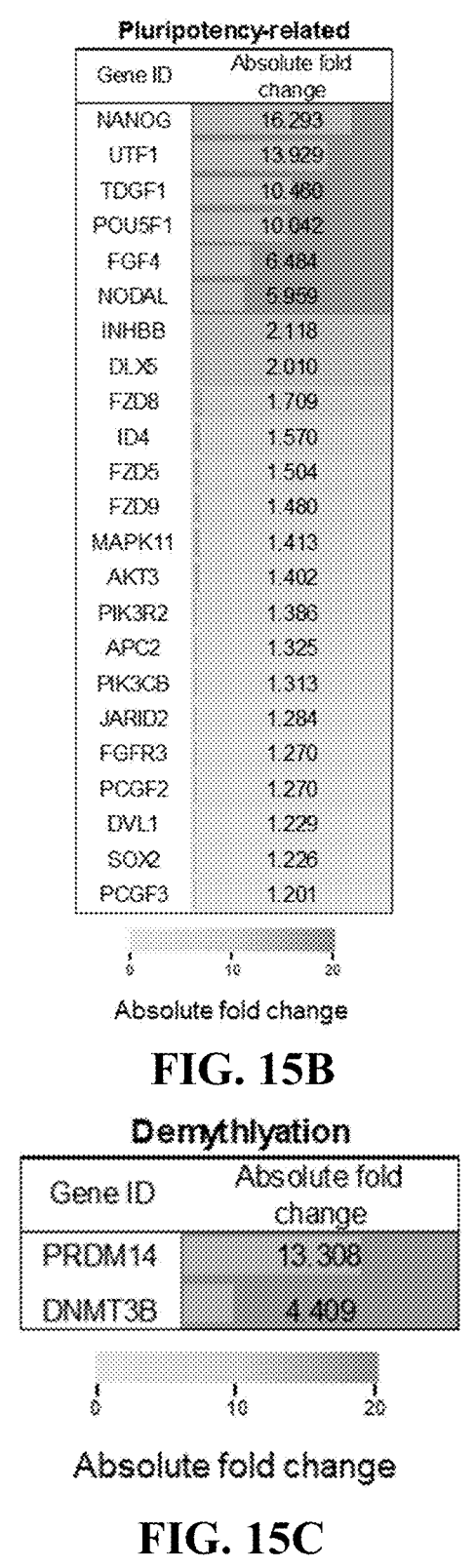

Pluripotency-related

| Gene ID | Absolute fold change |
|---------|----------------------|
| NANOG | 16.293 |
| UTF1 | 13.929 |
| TDGF1 | 10.460 |
| POU5F1 | 10.042 |
| FGF4 | 6.464 |
| NODAL | 5.959 |
| INHBB | 2.118 |
| DLX5 | 2.010 |
| FZD8 | 1.709 |
| ID4 | 1.570 |
| FZD5 | 1.504 |
| FZD9 | 1.480 |
| MAPK11 | 1.413 |
| AKT3 | 1.402 |
| PIK3R2 | 1.386 |
| APC2 | 1.325 |
| PIK3CB | 1.313 |
| JARID2 | 1.284 |
| FGFR3 | 1.270 |
| PCGF2 | 1.270 |
| DVL1 | 1.229 |
| SOX2 | 1.226 |
| PCGF3 | 1.201 |

Absolute fold change

FIG. 15B

Demythlyation

| Gene ID | Absolute fold change |
|---------|----------------------|
| PRDM14 | 13.308 |
| DNMT3B | 4.409 |

Absolute fold change

FIG. 15C

Absolute fold change

Pan neuronal markers

| Gene ID | Absolute fold change |
|---------|----------------------|
| MAP2 | 1.398 |
| DCX | 1.359 |
| NCAM1 | 1.502 |
| MAPT | 1.518 |

Absolute fold change

FIG. 15D

Forebrain markers

| Gene ID | Absolute fold change |
|---------|----------------------|
| GSX2 | 2.227 |
| FOXG1 | 2.138 |
| TBR1 | 1.930 |
| EMX1 | 1.895 |

Absolute fold change

FIG. 15E

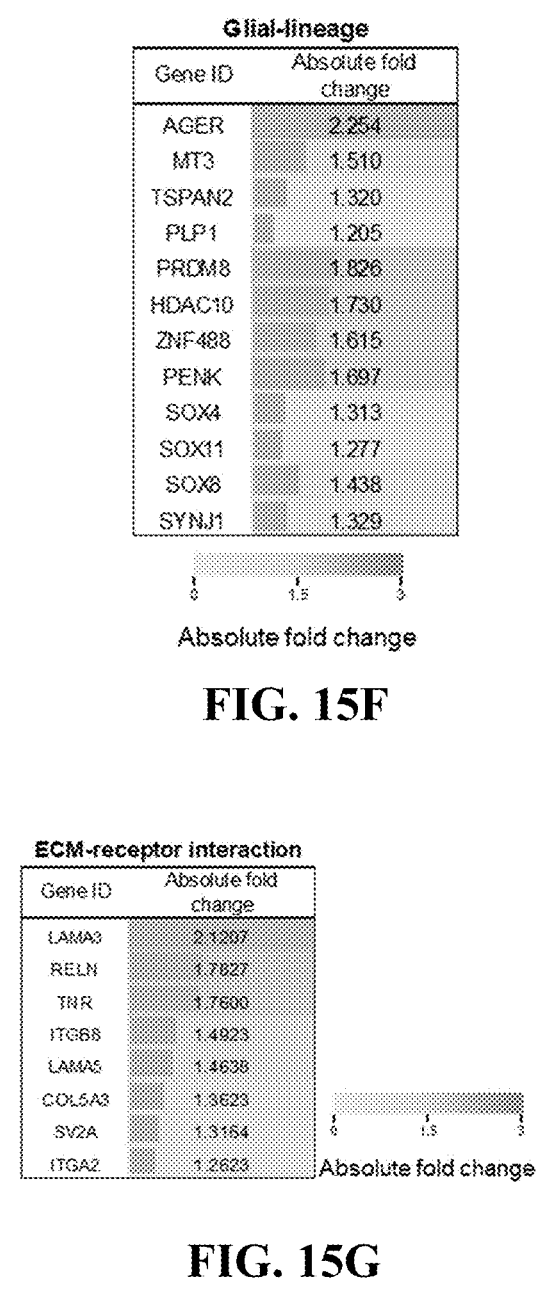

Glial-lineage

| Gene ID | Absolute fold change |
|---------|---------------------|
| AGER | 2.254 |
| MT3 | 1.510 |
| TSPAN2 | 1.320 |
| PLP1 | 1.205 |
| PRDM8 | 1.826 |
| HDAC10 | 1.730 |
| ZNF488 | 1.615 |
| PENK | 1.697 |
| SOX4 | 1.313 |
| SOX11 | 1.277 |
| SOX8 | 1.438 |
| SYNJ1 | 1.329 |

Absolute fold change

FIG. 15F

ECM-receptor interaction

| Gene ID | Absolute fold change |
|---------|---------------------|
| LAMA3 | 2.1207 |
| RELN | 1.7827 |
| TNR | 1.7600 |
| ITG68 | 1.4823 |
| LAMA5 | 1.4638 |
| COL5A3 | 1.3623 |
| SV2A | 1.3164 |
| ITGA2 | 1.2623 |

Absolute fold change

FIG. 15G

Cell adhesion

| Gene ID | Absolute fold change |
|---------|----------------------|
| NRXN3 | 1.6577 |
| CLDN6 | 1.6435 |
| CDH4 | 1.6072 |
| NRXN1 | 1.5346 |
| NCAM1 | 1.5024 |
| NLGN1 | 1.4973 |
| ITGB8 | 1.4923 |
| NCAM2 | 1.4617 |
| NRXN2 | 1.4114 |
| NEGR1 | 1.3886 |
| F11R | 1.3672 |
| VCAN | 1.3206 |
| NFASC | 1.2849 |
| L1CAM | 1.2848 |
| NRCAM | 1.2807 |
| CADM3 | 1.2676 |

Absolute fold change

FIG. 15H

Cellular binding

| Gene ID | Absolute fold change |
|---------|----------------------|
| SHB | 1.4746 |
| RGMA | 1.4645 |
| STX1A | 1.4485 |
| MINK1 | 1.3838 |
| PIK3CB | 1.3135 |
| CDH13 | 1.4957 |
| SFRP1 | 1.4491 |
| ACTN2 | 1.9204 |
| ICAM5 | 1.6791 |
| LAMA5 | 1.4838 |
| SEMA7A | 1.3245 |
| ITGA2 | 1.2623 |
| ADAM22 | 1.2465 |
| THY1 | 1.2450 |
| ITGB1BP1 | 1.2255 |

Absolute fold change

COMPOSITION FOR CULTURING BRAIN ORGANOID BASED ON DECELLULARIZED BRAIN MATRIX AND METHOD FOR PREPARING SAME

TECHNICAL FIELD

The present invention relates to a composition for culturing a brain organoid using a decellularized brain matrix and a method for preparing the same.

BACKGROUND ART

Decellularization of tissues and organs has been studied as a promising approach for preparing a functional support or scaffold for cell culture and transplantation.

During a decellularization process, cellular components are removed from the tissue, but the extracellular matrix and some growth factor proteins are preserved.

Therefore, various extracellular matrix components, which are preserved in the decellularized tissue including collagen, fibronectin, and laminin, provide a three-dimensional microenvironment similar to the inside of intact tissue, and thus can improve survival, proliferation, and differentiation of cultured cells.

Additionally, removal of cellular components alters the decellularized matrix into a functional scaffold with minimal immunogenicity for cell transplantation.

Recently, studies for functional tissue-engineered scaffold, which are obtained by applying several types of decellularized matrices derived from the brain, heart, blood vessels, heart valve, lungs, and kidneys, have been conducted.

In particular, the brain is an organ that serves as a major control tower for regulating an organism, and is an important organ that functions through a close network between neurons and other various cells. However, due to the complicated structure and working principle of the brain, sufficient studies have not been conducted, and studies for causes of neurological diseases and development of new drugs are confronted with limitations.

Therefore, there is a growing need for active studies of brain development and brain diseases through the construction of an in vitro model system that recapitulates the brain tissue and functions thereof, and new studies for producing miniature organs using human stem cell-derived organoids are in the spotlight.

Nevertheless, the brain organoid produced by the current technique of culturing an organoid has many differences from the actual brain tissue in terms of degree of differentiation and function, and there is a need for the development of an elementary technique for culture of a more mature brain organoid.

DISCLOSURE

Technical Problem

The present invention has been made to solve the above-mentioned problems of the prior art, and an object thereof is to provide a three-dimensional culture platform for improving immature structural development and immature differentiation of a brain organoid according to current culture techniques and for producing a brain organoid similar to the actual brain.

Technical Solution

According to an aspect of the present invention, there is provided a method for preparing a composition for culturing a brain organoid, comprising (a) decellularizing brain tissue; (b) drying the brain tissue; and (c) gelating the brain tissue.

In an embodiment, in the (c), the brain tissue and Matrigel® (basement membrane matrix secreted by Engelbreth-Holm-Swarm (EHS) mouse sarcoma cells) may be mixed to obtain a hydrogel.

In an embodiment, the hydrogel may contain a decellularized brain extracellular matrix (dBEM) in an amount of 0.01 to 2.0 mg/mL.

In an embodiment, in the (a), the brain tissue may be stirred in a decellularizing solution.

In an embodiment, the brain tissue may be stirred for 3 to 24 hours.

In an embodiment, 95% or more of cells of the brain tissue may be removed by the decellularization.

According to another aspect of the present invention, there is provided a hydrogel composition for culturing a brain organoid, comprising a decellularized brain extracellular matrix (dBEM).

In an embodiment, the composition may further comprise Matrigel® (basement membrane matrix secreted by Engelbreth-Holm-Swarm (EHS) mouse sarcoma cells).

In an embodiment, the decellularized brain extracellular matrix (dBEM) may have a concentration of 0.01 to 2.0 mg/mL.

In an embodiment, the composition may have an elastic modulus at 1 Hz of 100 to 150 Pa.

According to still another aspect of the present invention, there is provided a method for culturing a brain organoid in the composition.

Advantageous Effects

Unlike conventional techniques for culturing a brain organoid, the present invention is highly likely to be applied as an in vitro model for realizing actual brain tissue.

The brain matrix-based hydrogel of the present invention can promote differentiation of a brain organoid into neurons and cortical layer neurons, and can be usefully used for the construction of an in vitro model in a brain tissue-like form.

It should be understood that the effects of the present invention are not limited to the above-mentioned effects and include all effects which can be deduced from the detailed description of the present invention or the constitution of the invention described in the claims.

DESCRIPTION OF DRAWINGS

FIGS. 2A, 2B and 2C illustrate the results of the production and analysis of human decellularized brain tissue.

FIGS. 3A and 3B illustrate the results obtained by analyzing components of the decellularized brain tissue.

FIGS. 7A-7D, 8A-8C, and 9A-9B illustrate identification of the neuronal differentiation, structural maturation, and degree of development of a brain organoid cultured using the decellularized brain tissue-based hydrogel or Matrigel® (basement membrane matrix secreted by Engelbreth-Holm-Swarm (EHS) mouse sarcoma cells).

FIGS. 10A-10G illustrate the results obtained by comparatively analyzing the functionality of a brain organoid cultured using the decellularized brain tissue-based hydrogel or Matrigel® (basement membrane matrix secreted by Engelbreth-Holm-Swarm (EHS) mouse sarcoma cells).

FIGS. 12A-12G illustrate the results obtained by comparatively analyzing cortical layer development in a brain organoid cultured using the decellularized brain tissue-based hydrogel or Matrigel® (basement membrane matrix secreted by Engelbreth-Holm-Swarm (EHS) mouse sarcoma cells).

FIG. 14 illustrates the results obtained by qPCR analysis of gene expression of a brain organoid cultured using the decellularized brain tissue-based hydrogel.

FIGS. 15A-15I, FIG. 16 and FIG. 17 illustrate the results obtained by gene ontology (GO) analysis of gene expression of a brain organoid cultured using the decellularized brain tissue-based hydrogel.

MODES OF THE INVENTION

Figures 1A, 1B:
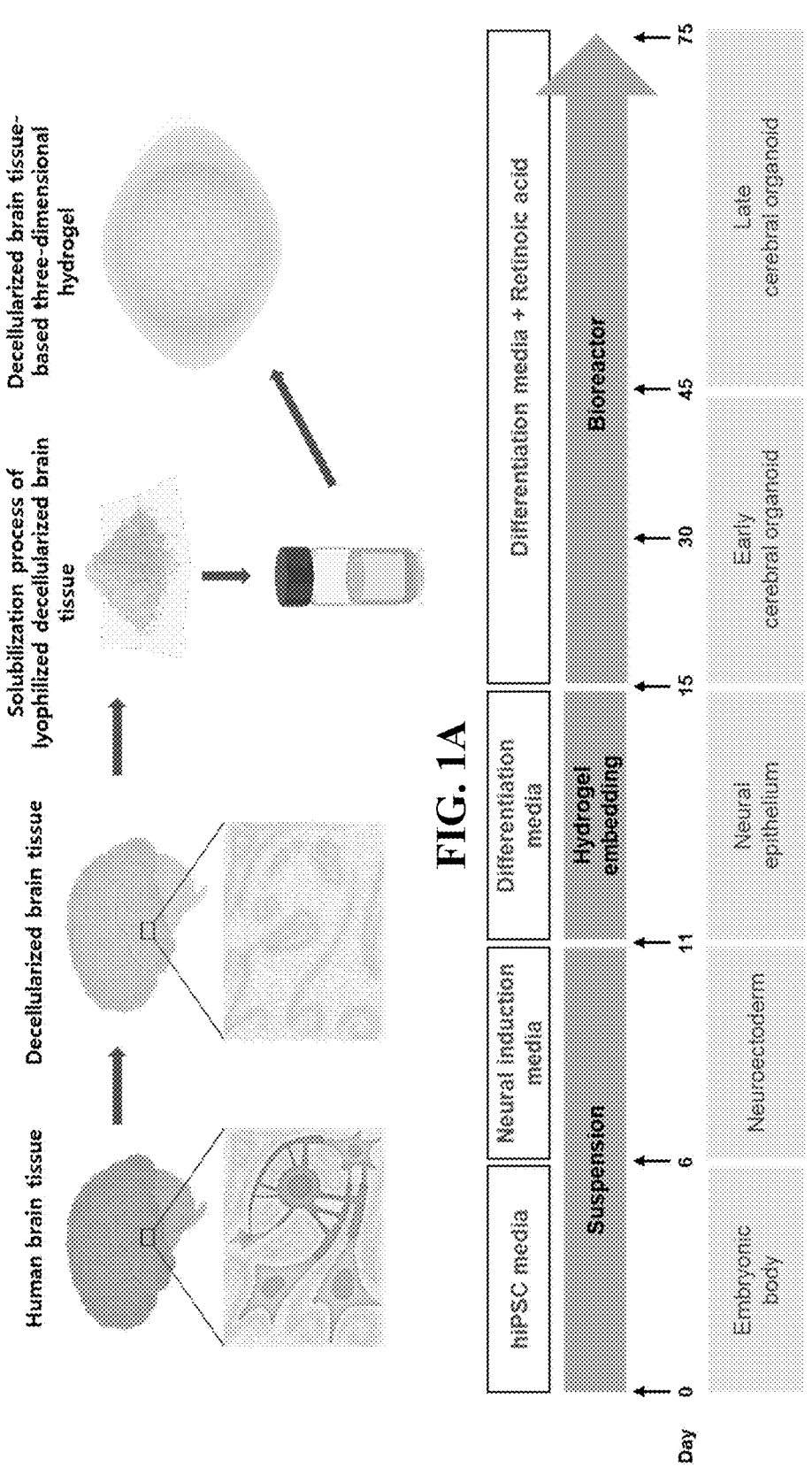
FIGS. 1A and 1B illustrate schematic diagrams for a method of producing a brain organoid using a decellularized brain tissue-based three-dimensional hydrogel.

Hereinafter, the present invention will be described with reference to the accompanying drawings. The present invention may, however, be embodied in many different forms, and thus should not be limited to the embodiments set forth herein. In a case where a certain entity "comprises" a certain constitutional element, unless specifically stated otherwise, the case means that the entity may further include other constitutional elements rather than excluding the other constitutional elements.

Unless otherwise defined, practice of the present invention involves performing conventional techniques commonly used in molecular biology, microbiology, protein purification, protein engineering and DNA sequencing, and the field of recombinant DNA within the skill of those skilled in the art. The techniques are known to those skilled in the art and are described in numerous standardized textbooks and reference books.

Unless otherwise defined herein, all technical and scientific terms used have the same meanings as commonly understood by those skilled in the art.

Various scientific dictionaries that include the terms included herein are well known and available in the art. Although any method and material similar or equivalent to those described herein find use in the practice or testing of the present invention, some methods and materials are described. The present invention is not limited to particular methodology, protocols, and reagents, as these may vary depending upon the context to be used by those skilled in the art. Hereinafter, the present invention will be described in more detail.

According to an aspect of the present invention, there is provided a method for preparing a composition for culturing a brain organoid, comprising (a) decellularizing brain tissue; (b) drying the brain tissue; and (c) gelating the brain tissue.

The composition contains a three-dimensional culture hydrogel prepared on the basis of a brain matrix composition obtained by decellularization, and can be effectively used for culturing a brain organoid.

The decellularized brain tissue contains actual tissue-specific extracellular matrix components, and thus can provide the physical, mechanical, and biochemical environment of the tissue in question, and is highly efficient in enhancing differentiation into brain tissue cells and tissue-specific functionality.

The "organoid" refers to an ultraminiature body organ obtained by culturing cells derived from the tissue or pluripotent stem cells in a 3D form to produce a form such as an artificial organ.

The organoid is a three-dimensional tissue analog that contains organ-specific cells which originate from stem cells and self-organize (or self-pattern) in a similar manner to the in vivo condition. The organoid can be developed into a specific tissue by restricted element (for example, growth factor) patterning.

The organoid can have the original physiological characteristics of the cells and can have an anatomical structure that mimics the original state of a cell mixture (including all remaining stem cells and the neighboring physiological niche as well as limited cell types). A three-dimensional culture method allows the organoid to be better arranged in terms of cell to cell functions, and to have an organ-like form with functionality and a tissue-specific function.

In the (b), the decellularized brain tissue containing the extracellular matrix may be air-dried or lyophilized. After drying, the decellularized brain tissue may be finally sterilized by being exposed to ethylene oxide gas or supercritical carbon dioxide by an electron beam or gamma radiation. The decellularized brain tissue may be stored, packaged or dispersed in a lyophilized state.

The sterilized decellularized brain tissue may be solubilized in an acidic solution with a protease such as pepsin or trypsin. The resultant may be mixed with a base such as an isotonic buffer or NaOH for neutralization so that a pH thereof is adjusted to 7.2 to 7.8, and may be gelated at a temperature of 25° C. to 38° C.

In the (c), the brain tissue and Matrigel® (basement membrane matrix secreted by Engelbreth-Holm-Swarm (EHS) mouse sarcoma cells) may be mixed to obtain a hydrogel.

The "Matrigel®" is a protein complex (product name of BD Biosciences) extracted from Engelbreth-Holm-Swarm (EHS) mouse sarcoma cells, and may contain extracellular matrix components such as laminin, collagen, and heparan sulfate proteoglycan, and fibroblast growth factor (FGF), epidermal growth factor (EGF), insulin-like growth factor (IGF), transforming growth factor-beta (TGF-β), or platelet-derived growth factor (PDGF).

The "hydrogel" is a material in which a liquid that contains water as a dispersion medium is hardened, through the sol-gel phase transition, to lose fluidity and to form a porous structure. The hydrogel can be formed by causing a hydrophilic polymer that has a three-dimensional network structure and a microcrystalline structure to contain water and to be expanded.

The hydrogel may contain the decellularized brain tissue and Matrigel® (basement membrane matrix secreted by Engelbreth-Holm-Swarm (EHS) mouse sarcoma cells) in a predetermined ratio, and the hydrogel may contain the decellularized brain extracellular matrix (dBEM) in an amount of 0.01 to 2.0 mg/mL.

The "extracellular matrix" refers to a natural support for cell growth which is prepared through decellularization of the tissue found in mammals and multicellular organisms. The extracellular matrix may be further treated through dialysis or crosslinking.

The extracellular matrix may be a mixture of structural or non-structural biomolecules including, but not limited to, collagen, elastins, laminins, glycosaminoglycans, proteoglycans, antimicrobials, chemoattractants, cytokines, and growth factors.

The extracellular matrix may take various forms in mammals and contain collagen in an amount of about 90%. Extracellular matrices derived from a variety of body tissues may be different in total structure and composition due to their inherent role required for each tissue. The decellularized brain extracellular matrix may be contained at a concentration of 0.01 to 2.0 mg/mL by being mixed with the decellularized brain tissue in an appropriate ratio.

The "derive" or "derived" refers to components obtained from mentioned sources by useful methods.

For example, the extracellular matrix-derived gel refers to a gel containing extracellular matrix components obtained from the tissue by a variety of technically known methods for isolating the extracellular matrix. Alternatively, the decellularized brain extracellular matrix may refer to an extracellular matrix containing components obtained from the brain tissue by a useful method.

In the (a), the brain tissue may be stirred in a decellularizing solution.

In an embodiment, the brain tissue may be stirred for 3 to 24 hours, and 95% or more of cells of the brain tissue may be removed by the decellularization.

The "decellularizing solution" may contain various detergent components to remove the brain tissue cells, and examples thereof may include, but are not limited to, hypertonic saline, peracetic acid, Triton™ X-100 (2-[4-(2,4,4-trimethylpentan-2-yl)phenoxy]ethanol), SDS, or other detergent components.

The decellularized extracellular matrix may be dried, and may be, for example, lyophilized or air-dried.

The dried extracellular matrix may be comminuted by methods including tearing, milling, cutting, grinding and shearing. The comminuted extracellular matrix may be processed into a powder form by a method such as grinding or milling in a frozen or lyophilized state.

According to another aspect of the present invention, there is provided a hydrogel composition for culturing a brain organoid, comprising a decellularized brain extracellular matrix (dBEM).

Since the hydrogel composition contains the decellularized brain extracellular matrix in an appropriate ratio, the elastic modulus thereof can be maintained at a level similar to that in the actual brain tissue environment, and the optimum environment for culturing a brain organoid can be created at an elastic modulus at 1 Hz of 100 to 150 Pa.

According to still another aspect of the present invention, there is provided a method for culturing a brain organoid in the composition.

The existing Matrigel®-based culture system is an extract derived from animal cancer tissue, has a large difference between the batches, does not simulate the actual brain environment, and exhibits insufficient efficiency in differentiation or development into a brain organoid. On the other hand, the hydrogel composition can create a brain tissue-like environment, and thus is suitable for culturing a brain organoid.

The brain organoid cultured in the brain matrix-based hydrogel composition can promote not only differentiation into various neurons including cortical layer neurons, but also can be structurally developed into a form similar to the actual brain.

The culture refers to a process of maintaining and growing cells under suitable conditions, and the suitable conditions may refer, for example, to the temperature at which the cells are maintained, nutrient availability, atmospheric $CO_2$ content, and cell density.

Appropriate culture conditions for maintaining, proliferating, expanding, and differentiating different types of cells are known in the art and are documented. Suitable conditions for the formation of the organoid may be conditions that facilitate or allow for cell differentiation and formation of a multicellular structure.

Hereinafter, the present invention will be further described by way of examples. However, it is apparent that the present invention is not limited by the following examples.

Experimental Example 1: Production of Brain Organoid Using Decellularized Brain Extracellular Matrix (dBEM)-Based Three-Dimensional Hydrogel Referring to FIG. 1, a three-dimensional culture platform which is excellent in production efficiency of a brain organoid was prepared using a hydrogel containing a decellularized brain extracellular matrix (dBEM).

The dBEM contains tissue-specific extracellular matrix components, and thus provides cells in culture with a tissue-specific physical and biochemical microenvironment, so that production of an organoid and differentiation efficacy thereof can be enhanced.

The lyophilized dBEM was subjected to a solubilization process through an enzyme treatment method and utilized in hydrogel production (FIG. 1A).

A brain organoid can be formed in the dBEM-based hydrogel and cultured for a long period, through the culture protocol of FIG. 1B.

Experimental Example 2: Production and Analysis of Human Decellularized Brain Extracellular Matrix (dBEM)

Human brain tissue was cut to a size of 1×1×1 cm³, and decellularized by being stirred in decellularizing solutions in the following order.

First, stirring (60 rpm) was performed in distilled water for 24 hours, and stirring (60 rpm, 37° C.) was performed in 0.05% (v/v) trypsin/ethylenediaminetetraacetic acid (EDTA) (Thermo Fisher Scientific, Waltham, MA) for 90 minutes.

Stirring was performed for 120 minutes in 3% (v/v) Triton™ X-100 (2-[4-(2,4,4-trimethylpentan-2-yl)phenoxy]ethanol) (Wako, Osaka, Japan) containing 0.1% (v/v) ammonium hydroxide (Sigma, St. Louis, MO).

Stirring was performed in a 1M sucrose solution (Sigma) for 30 minutes, and stirring was performed in distilled water for 15 minutes.

Stirring was performed in 3% (v/w) sodium dodecyl sulfate (Sigma) for 60 minutes, and stirring was performed in 4% (v/v) ethanol (Sigma) for 120 minutes.

Stirring was performed in PBS (Sigma) for 15 minutes, and stirring (60 rpm) was performed in 1% (v/v) penicillin/ streptomycin (Thermo Fisher Scientific) for 60 minutes.

Finally, stirring was performed in distilled water for 15 minutes, and stirring was performed in PBS for 15 minutes.

At the time of replacing each solution, the existing solution was washed with distilled water. Unless otherwise indicated, all procedures were carried out at 4° C. and decellularization was performed by stirring at 120 rpm.

Referring to FIG. 2, cells can be efficiently removed through the decellularization process, and the decellularized brain extracellular matrix (dBEM) in which the matrix tissue is mostly maintained can be secured.

Histology (H&E staining, Masson's trichrome staining; MT staining) analysis showed that the cells are removed from the tissue after being subjected to the decellularization process, while the extracellular matrix components simulating the biochemical microenvironment are retained (FIG. 2A).

DNA was quantified, and as a result, most of the cells (98% or more) were removed from the tissue (FIG. 2B).

Glycosaminoglycan (GAG) was quantified, and as a result, most of the GAG components were retained in the tissue without loss after the decellularization process (FIG. 2C).

Experimental Example 3: Analysis of Hydrogel Components

Immunofluorescence staining and mass spectrometry were used to analyze brain tissue-derived extracellular matrix components that can affect the formation of an organoid.

Referring to FIG. 3, subtypes of laminin, which is an important factor for the development and differentiation of cells in brain tissue (before decellularization) were analyzed through immunostaining, and as a result, in particular, laminin subtypes $\alpha 5$, $\beta 1$, and $\gamma 1$ were abundantly present (FIG. 3A).

Mass spectrometry was used to analyze protein components in the decellularized brain tissue, and as a result, not only various types of collagens and glycoproteins such as fibronectin, and laminin but also proteoglycan and lipid components were abundantly contained (FIG. 3B).

In other words, the dBEM hydrogel was evaluated to enhance the formation and differentiation of a brain organoid based on biochemical components that simulate a brain tissue-specific microenvironment.

Experimental Example 4: Analysis of Mechanical Properties

Figure 4:
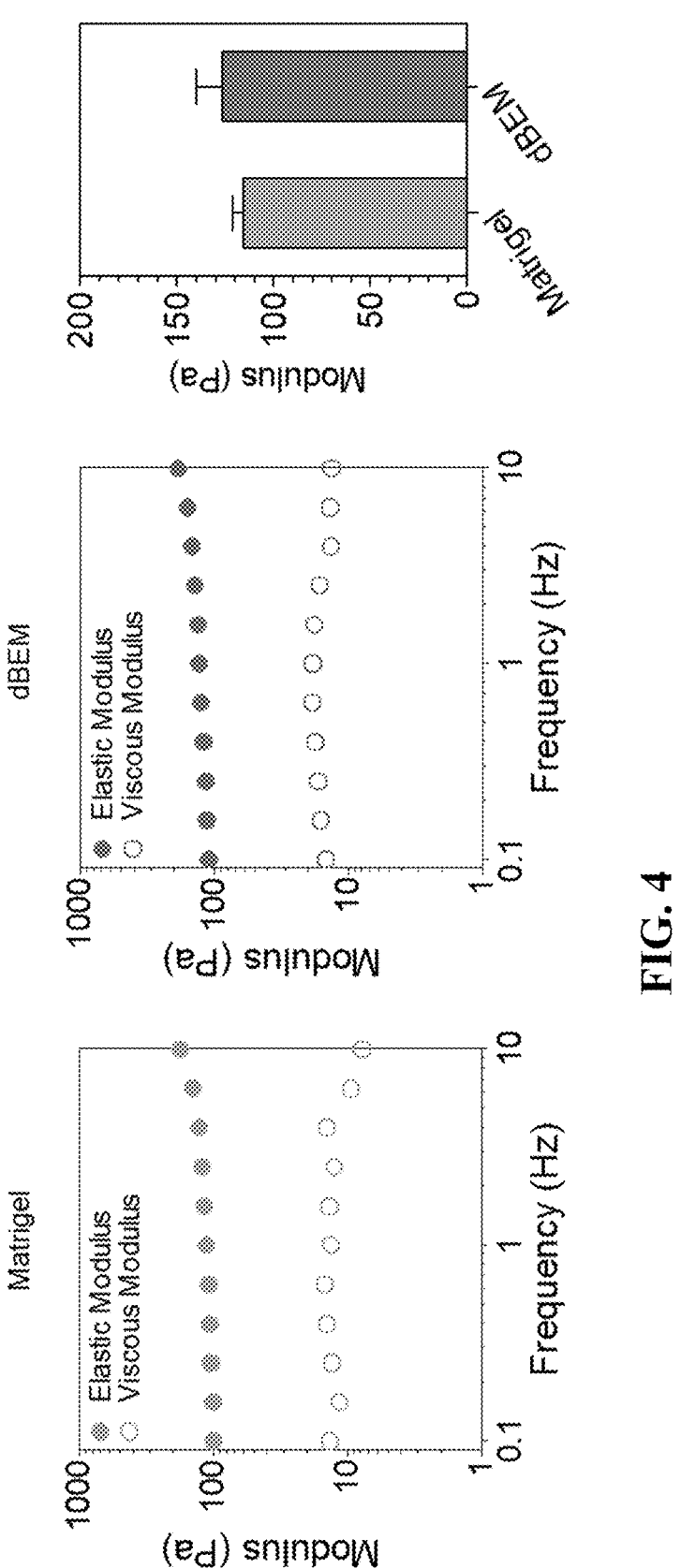
FIG. 4 illustrates the results obtained by analyzing mechanical properties of the decellularized brain tissue-based hydrogel.

Referring to FIG. 4, a dBEM hydrogel having a concentration of 400 µg/mL was produced by incorporating a dBEM component into Matrigel® (basement membrane matrix secreted by Engelbreth-Holm-Swarm (EHS) mouse sarcoma cells) which is widely used for the production of an organoid.

The physical properties of the Matrigel® (basement membrane matrix secreted by Engelbreth-Holm-Swarm (EHS) mouse sarcoma cells) hydrogel and the dBEM hydrogel were comparatively analyzed using a rheometer. As a result, the elastic modulus was measured to be higher than the viscous modulus within the measurement frequency, indicating that a stable hydrogel was formed.

As a result of comparing the elastic moduli at 1 Hz, Matrigel® (basement membrane matrix secreted by Engelbreth-Holm-Swarm (EHS) mouse sarcoma cells) had an elastic modulus of about 115 Pa and the dBEM had an elastic modulus of about 126 Pa, indicating that there was no significant change in physical properties of the hydrogel due to the addition of dBEM.

Experimental Example 5: Analysis of Tissue-Specific Effects of Hydrogel

Referring to FIG. 5, tissue-specific three-dimensional hydrogels were produced using decellularized extracellular matrices derived from a variety of tissues, and brain tissue-specific functionality of the dBEM hydrogels was identified.

Figure 5A:
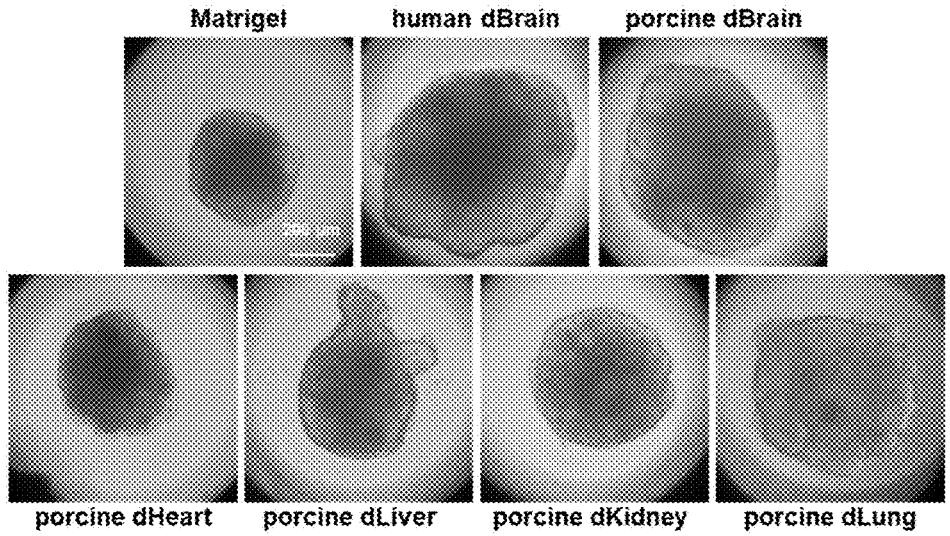
FIGS. 5A and 5B illustrate the results obtained by analyzing tissue-specific effects of the decellularized brain tissue-based hydrogel.

Three-dimensional culture of a brain organoid derived from human induced pluripotent stem cells (iPSCs) was performed. As a result, the brain organoid exhibited a larger size in a case of being cultured in the dBEM hydrogel than in a case of being cultured in Matrigel® (basement membrane matrix secreted by Engelbreth-Holm-Swarm (EHS) mouse sarcoma cells) (at an initial stage of culture, on day 20), and clear neural tube formation which is important for the formation of the early brain organoid and a high cell density were exhibited (FIG. 5A).

Figure 5B:
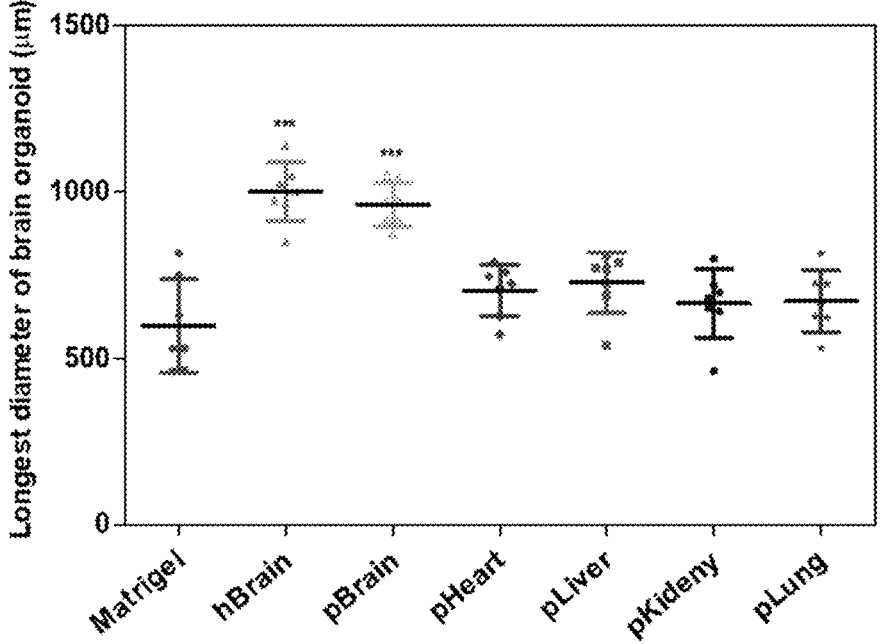

The size of the brain organoid cultured in each hydrogel was quantified. As a result, the brain organoid grown in the dBEM hydrogel exhibited the largest size, and it was analyzed that the brain tissue-specific dBEM hydrogel is effective for culture of a brain organoid (FIG. 5B).

Experimental Example 6: Identification of Neuronal Differentiation of Brain Organoid Referring to FIG. 6, the brain organoid was cultured for 30 days using the dBEM hydrogel, and an analysis with respect to the degree of differentiation and development inside the organoid was performed.

Immunofluorescence staining was used to analyze differentiation into a neuronal lineage.

Figure 6A:
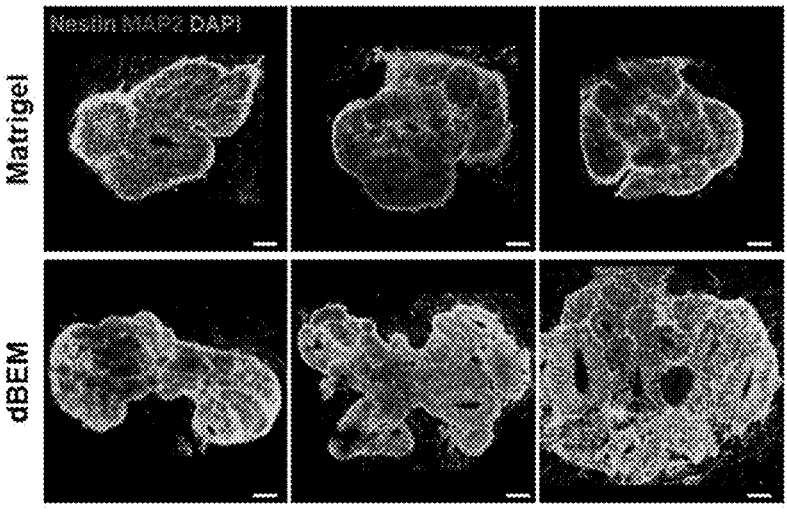
FIGS. 6A, 6B, 6C and 6D illustrate the results obtained by comparatively analyzing the neuronal differentiation of a brain organoid cultured using the decellularized brain tissue-based hydrogel or Matrigel® (basement membrane matrix secreted by Engelbreth-Holm-Swarm (EHS) mouse sarcoma cells).
Figure 6B:
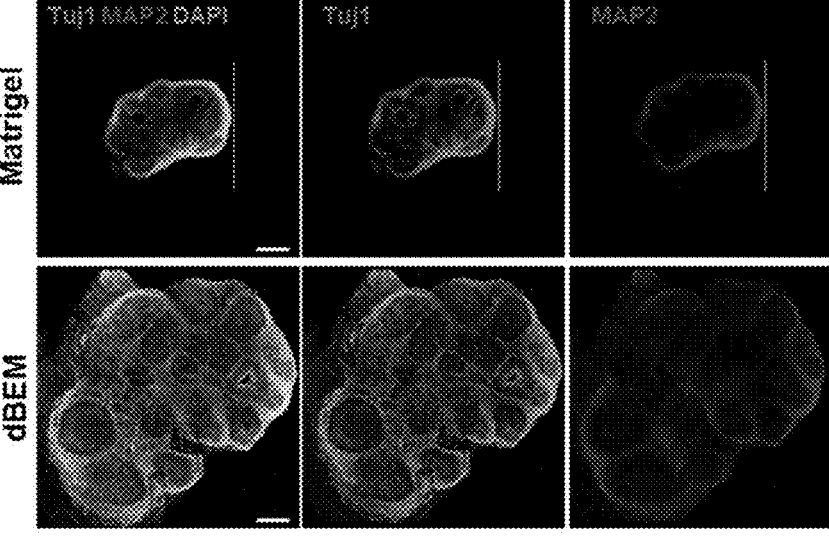

The organoid differentiated in the dBEM hydrogel exhibited increased expression of the neural stem cell marker (Nestin) and mature neuron markers (Tuj1, MAP2) as compared with the organoid differentiated in Matrigel® (basement membrane matrix secreted by Engelbreth-Holm-Swarm (EHS) mouse sarcoma cells) (FIGS. 6A and 6B).

Figure 6C:
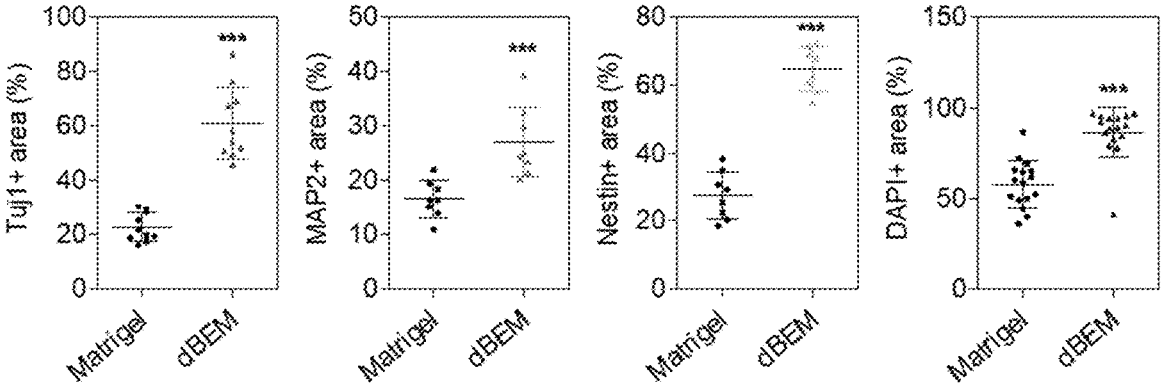
Figure 6D:
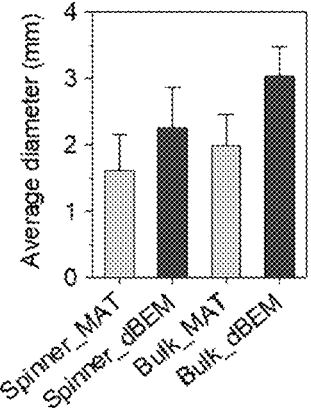

The image-based analysis showed that the dBEM hydrogel promotes not only the differentiation of neurons but also the proliferation of neural stem cells and the development of the brain organoid (FIGS. 6C and 6D).

In particular, the brain organoid cultured in the dBEM hydrogel exhibited an increased size regardless of the culture environment (spinner flask, multiwell plate) (FIG. 6D).

Experimental Example 7: Identification of Differentiation and Development of Brain Organoid The brain organoid was cultured for 30 days using the dBEM hydrogel, and an analysis with respect to the degree of differentiation and development was performed.

Immunofluorescence staining was used to analyze the expression of neuron markers (Tuj1, NeuN, MAP2), a dorsal marker of early brain development Pax6, a marker (FoxG1) corresponding to the forebrain, and a stem cell marker (Sox2) (FIG. 7).

The brain organoid cultured in the dBEM hydrogel exhibited not only increased differentiation into neurons but also increased production of stem cells, so that the maturation of the brain organoid was promoted and a size thereof was also significantly increased (FIG. 7A).

In addition, histology and SEM analysis also showed increased cell density in the brain organoid (FIG. 7B), decreased void space in the brain organoid (FIG. 7C), and formation of a mature organoid in the dBEM hydrogel.

In particular, the laminin layer corresponding to the basal lamina of the human brain was more clearly formed in the brain organoid cultured in the dBEM (FIG. 7D).

The brain organoid was cultured for 45 days using the dBEM hydrogel, and the degree of differentiation and development thereof was analyzed.

Figure 8A:
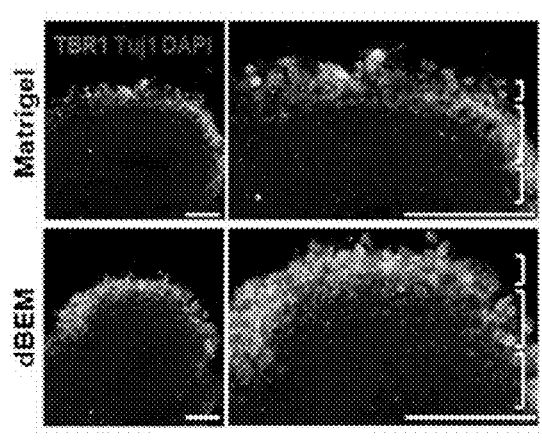
Figure 8B:
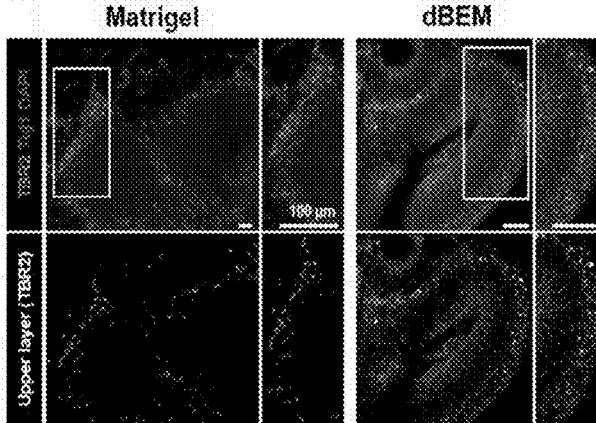

Referring to FIG. 8, the staining of the cortical layer markers TBR1 and TBR2 showed that the number of cells expressing the markers is increased and the thickness of the layer of expressing cells is increased, as compared with the existing Matrigel® (basement membrane matrix secreted by Engelbreth-Holm-Swarm (EHS) mouse sarcoma cells) culture environment (FIGS. 8A and 8B).

Figure 8C:
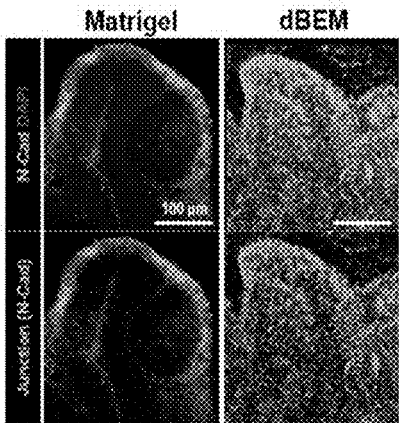

In addition, it was identified that the interaction (N-cadherin) between the neurons is promoted (FIG. 8C).

The brain organoid was cultured for 45 days using Matrigel® (basement membrane matrix secreted by Engelbreth-Holm-Swarm (EHS) mouse sarcoma cells) or the dBEM hydrogel, and the distribution and structure development of three-dimensional neurons in the brain organoid were identified using a tissue clearing technique.

Figures 9A, 9B:
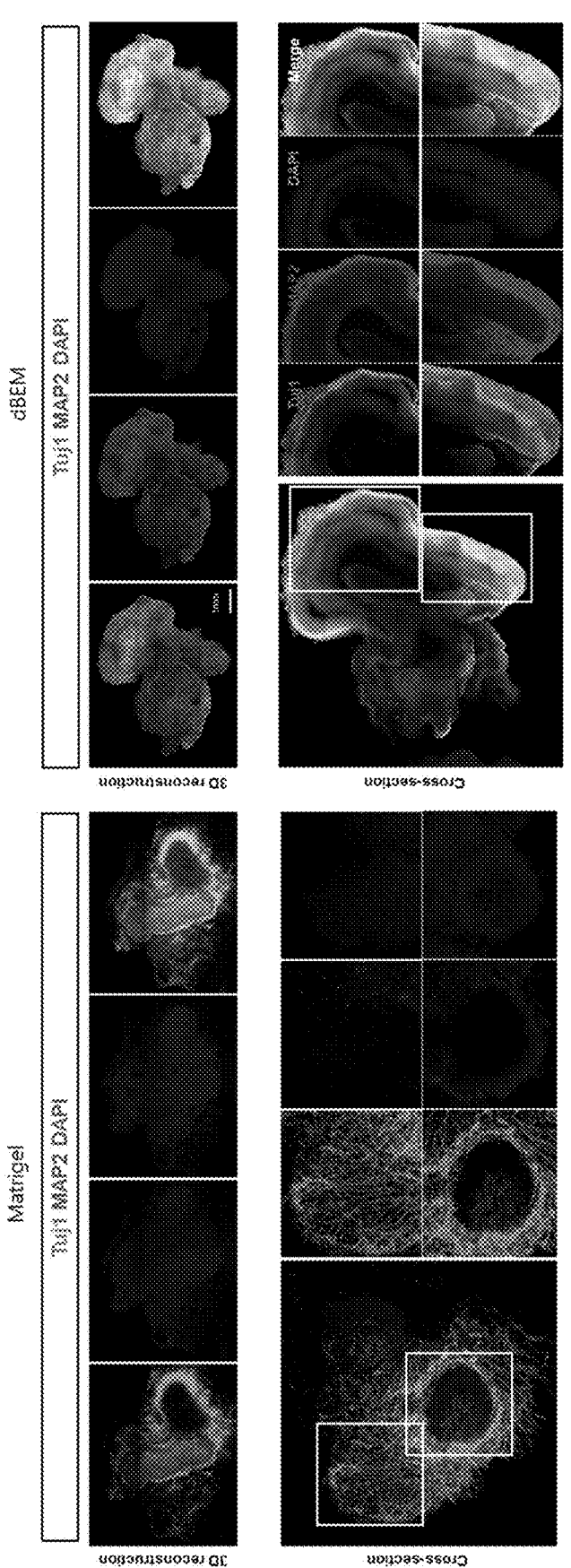

Referring to FIGS. 9A and 9B, in the brain organoid cultured using the dBEM hydrogel, increased differentiation into mature neurons was exhibited, and a brain tissue-specific wrinkled structure was developed in a form similar to the actual brain.

Experimental Example 8: Analysis of Functionality of Brain Organoid

Fluorescent calcium imaging experiments were carried out to identify the reactivity of the brain organoid, which had been cultured in the hydrogel for 45 days, to the glutamate and gamma amino butyric acid (GABA) neurotransmitters.

Figure 10A:
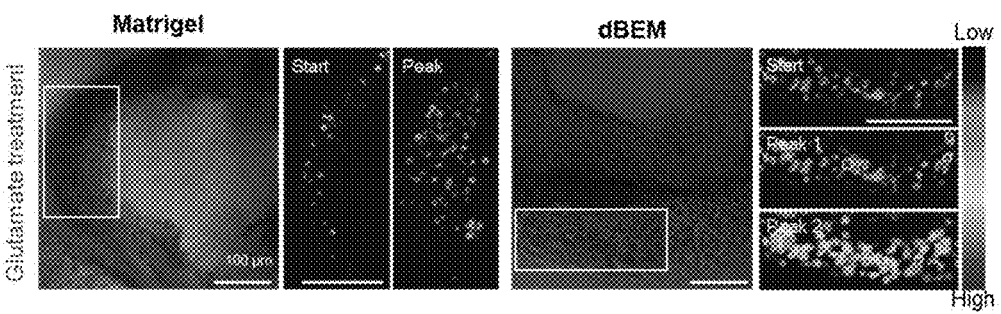

Referring to FIG. 10, the brain organoid cultured in the dBEM hydrogel was higher in the proportion of cells responsive to glutamate and intracellular calcium influx than the brain organoid cultured in Matrigel® (basement membrane matrix secreted by Engelbreth-Holm-Swarm (EHS) mouse sarcoma cells) (FIGS. 10A and 10D).

Figure 10B:
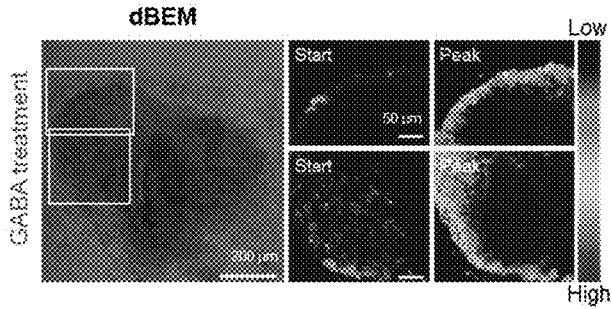

The brain organoid cultured in the dBEM also responded to gamma amino butyric acid, whereas no responsive cells were observed in the brain organoid cultured in Matrigel® (basement membrane matrix secreted by Engelbreth-Holm-Swarm (EHS) mouse sarcoma cells) (FIG. 10B).

Figure 10C:
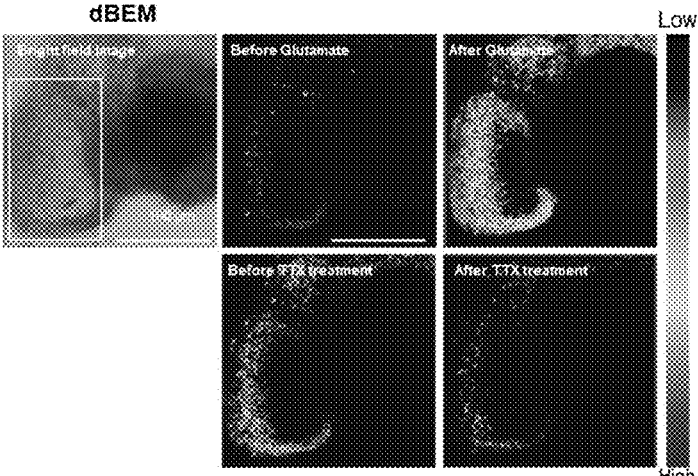

On the other hand, the brain organoid cultured in the dBEM hydrogel was observed to respond to glutamate, and exhibited a decreased neurotransmission signal and decreased activity in a case of being treated with the sodium channel blocker, tetrodotoxin (TTX) (FIG. 10C).

Figure 10G:
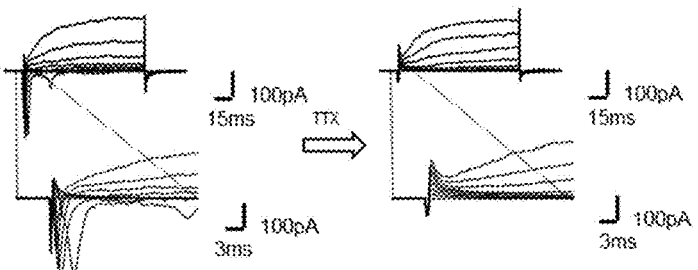

Patch clamps were used to analyze electrophysiological functionality of the brain organoid cultured in the dBEM hydrogel (FIGS. 10E to 10G).

In a voltage-clamped state, current generation by the voltage-openable sodium channel was identified (FIG. 10E), and the sodium channel-induced current disappeared due to the treatment with the Na+ channel blocker, tetrodotoxin (TTX) (FIG. 10G). In a case of being measured in a current-clamped state, an action potential was generated (FIG. 10F).

In other words, the brain organoid cultured under the dBEM condition exhibited remarkably superior neuroelectrophysiological functionality as compared with the brain organoid cultured under the Matrigel® (basement membrane matrix secreted by Engelbreth-Holm-Swarm (EHS) mouse sarcoma cells) condition.

Experimental Example 9: Identification of Differentiation of Brain Organoid and Intercellular Network Thereof After culture of the brain organoid was conducted for 75 days using Matrigel® (basement membrane matrix secreted by Engelbreth-Holm-Swarm (EHS) mouse sarcoma cells) as a control and the dBEM hydrogel, immunofluorescence staining was used to analyze the differentiation and intercellular network formation.

Referring to FIG. 11, the brain organoid cultured in the dBEM hydrogel exhibited remarkably high levels of expression and distribution of N-Cadherin, which is known to play a role in adhesion between neurons, as compared with the brain organoid cultured in Matrigel® (basement membrane matrix secreted by Engelbreth-Holm-Swarm (EHS) mouse sarcoma cells).

Figure 11A:
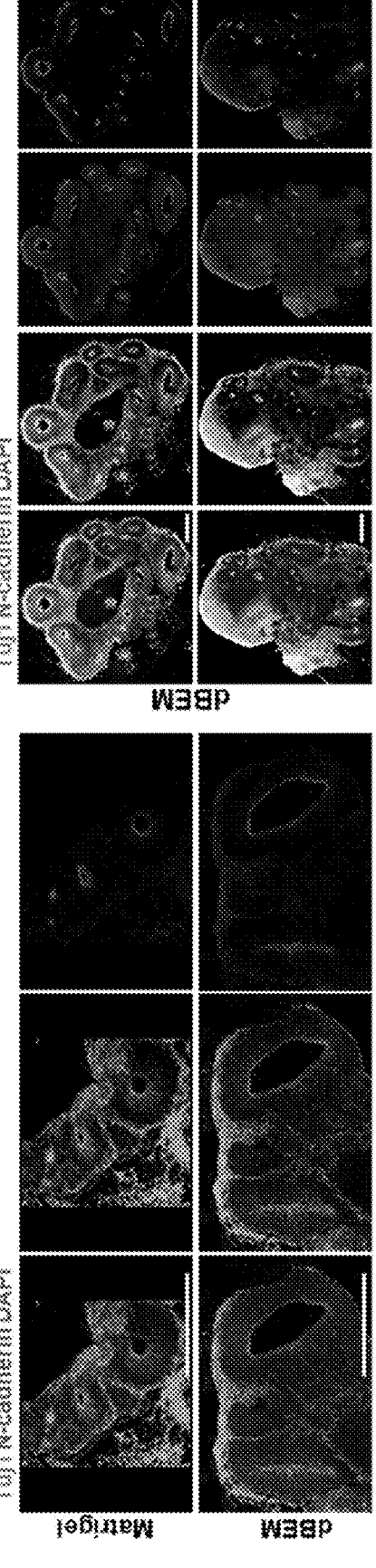
FIGS. 11A-11D illustrate the results obtained by comparatively analyzing the differentiation and intercellular network of a brain organoid cultured using the decellularized brain tissue-based hydrogel or Matrigel® (basement membrane matrix secreted by Engelbreth-Holm-Swarm (EHS) mouse sarcoma cells).
Figure 11B:
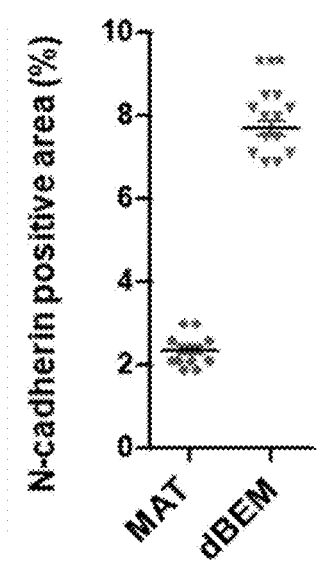

The N-cadherin is known to be a protein associated with promotion of neurite outgrowth and synaptogenesis (FIGS. 11A and 11B).

Immunofluorescence staining was used to analyze the expression of the synapsin I protein, a synaptic vesicle marker, in the brain organoid cultured under the dBEM condition.

Figure 11C:
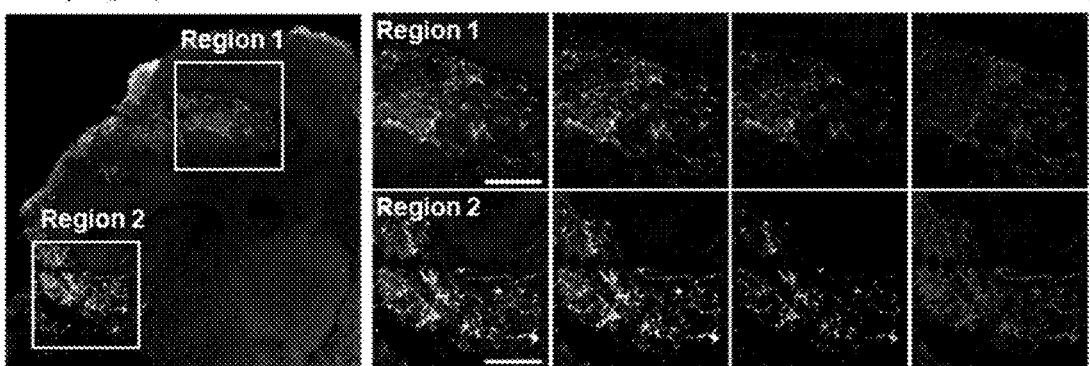

Synapsin I is an important protein in the chemical signaling process of neural synapses, and the results suggest that the brain organoid cultured using the dBEM exhibit a high degree of maturation (FIG. 11C).

Figure 11D:
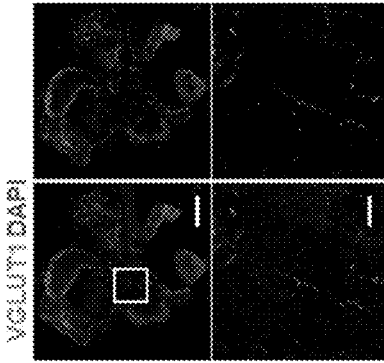

In addition, the expression of VGLUT, a representative marker of a glutamatergic neuron, showed a high degree of differentiation in the brain organoid cultured in the dBEM (FIG. 11D).

Experimental Example 10: Development of Cortical Layer in Brain Organoid

After the brain organoid was cultured for 75 days using Matrigel® (basement membrane matrix secreted by Engelbreth-Holm-Swarm (EHS) mouse sarcoma cells) or the dBEM hydrogel, a degree of development of the cortical layer in the brain organoid was analyzed.

Figure 12A:
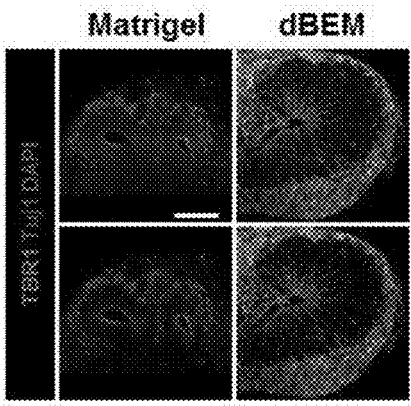
Figure 12B:
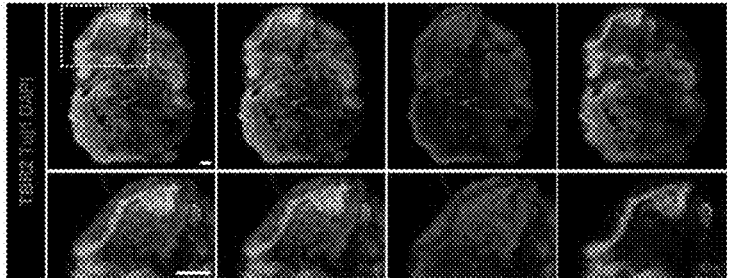

Referring to FIG. 12, the brain organoid cultured in the dBEM hydrogel exhibited increased expression and thickness of TBR1, a marker corresponding to the cortical layer IV position, and it was identified that differentiation into a mature brain organoid occurs (FIG. 12A).

Figure 12C:
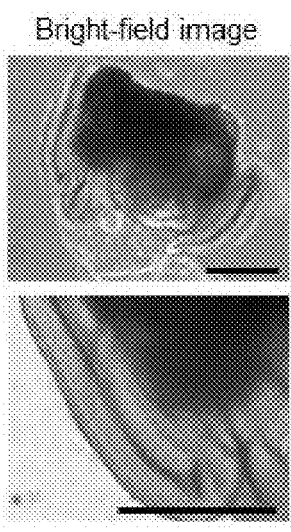

In the brain organoid cultured in the dBEM hydrogel, the expression of TBR2, a marker corresponding to the subventricular zone, was overall widely distributed (FIG. 12B), and the cortical layer and specific wrinkled structure of the brain organoid were well developed (FIG. 12C).

In a case where a size of the formed brain organoid is measured based on the longest diameter, the brain organoid cultured in the dBEM hydrogel exhibited a remarkably large size as compared with the brain organoid cultured in Matrigel® (basement membrane matrix secreted by Engelbreth- Holm-Swarm (EHS) mouse sarcoma cells) (FIG. 12D), and cortical layer markers were continuously expressed in the dBEM hydrogel (FIG. 12E).

In addition, two-dimensional and three-dimensional light-sheet microscopy was used to analyze the formed brain organoid. As a result, in the dBEM hydrogel group, the wrinkled structure of the brain organoid was developed and the total volume was increased (FIGS. 12F and 12G).

These results suggest that a degree of maturation of brain organoid can be increased by the dBEM hydrogel.

Experimental Example 11: Analysis of Development of Cortical Layer and Forebrain in Brain Organoid The brain organoid was cultured for 75 days using the dBEM hydrogel, and fluorescence immunostaining was used to analyze the maturation of the cortical layer and the development of the forebrain portion.

Figures 13A, 13B:
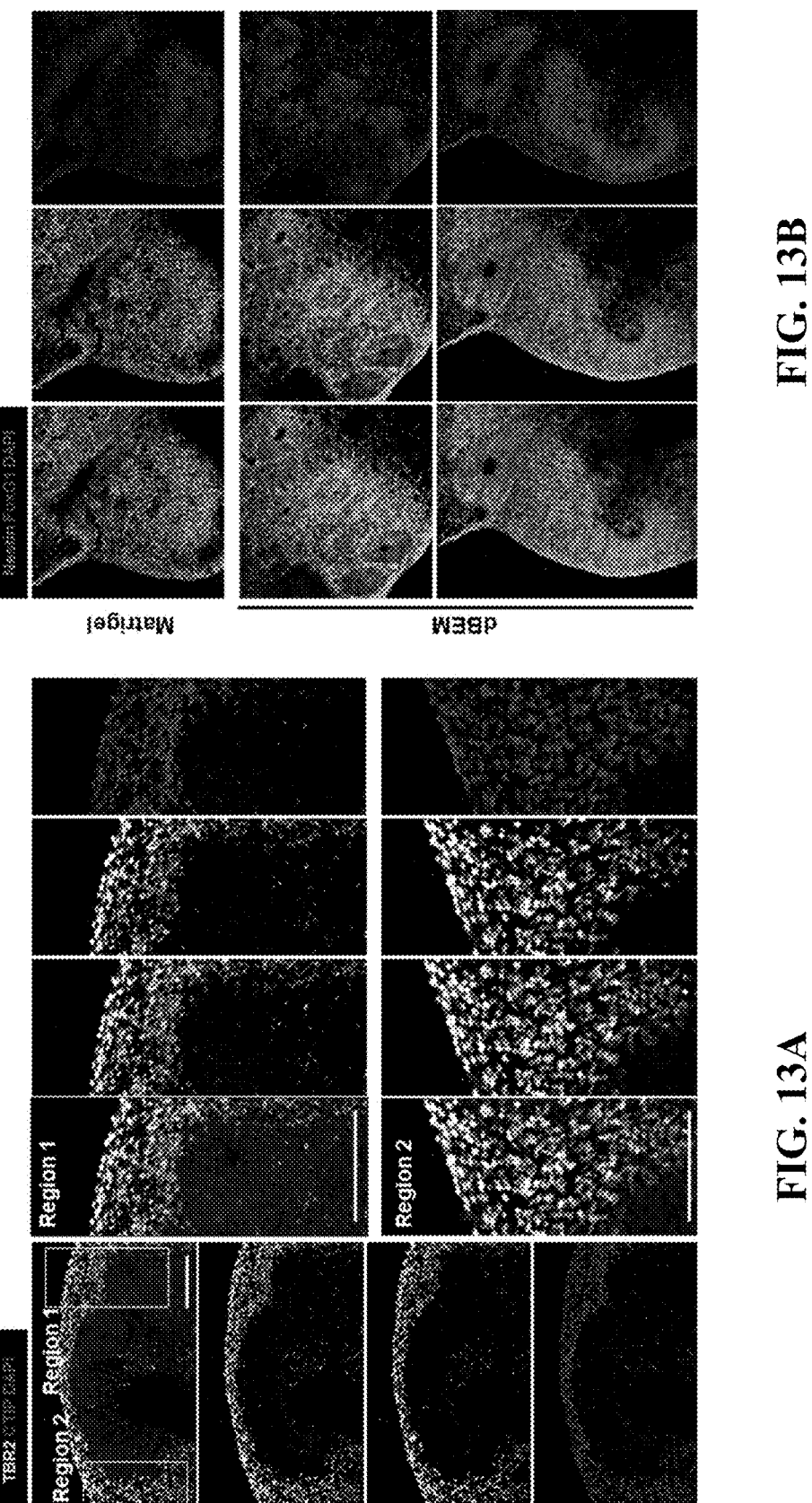
FIGS. 13A-13B illustrate the results obtained by comparatively analyzing cortical layer and forebrain development in a brain organoid cultured using the decellularized brain tissue-based hydrogel or Matrigel® (basement membrane matrix secreted by Engelbreth-Holm-Swarm (EHS) mouse sarcoma cells).

Referring to FIG. 13, the maturation and development of the cortical layer in the brain organoid cultured in the dBEM environment were identified through immunostaining of TBR2, a marker corresponding to the subventricular zone, and CTIP, a marker for cortical layer 5 (FIG. 13A).

In addition, in a case of comparing the overall distribution of FoxG1, a forebrain marker, the brain organoid cultured in the dBEM hydrogel exhibited a remarkably increased expression level of the forebrain-specific marker, and also exhibited an increased size and degree of maturation (FIG. 13B).

Experimental Example 12: Comparison of Gene Expression in Brain Organoid (lPCR)

The gene expression in the brain organoid which had been cultured in the hydrogel for 75 days was identified by qPCR, in which gene expression levels in the human fetal neural stem cell (hNSC) and human-derived brain tissue (hTissue) as controls were compared together.

Referring to FIG. 14, in a case of the brain organoid cultured using the dBEM, increased expression of Tuj1, a neuron marker, and TH, a dopaminergic neuron marker, were exhibited, and increased expression of CDH1 that plays an important role in intercellular adhesion and neuron survival was also exhibited, as compared with the brain organoid cultured in Matrigel® (basement membrane matrix secreted by Engelbreth-Holm-Swarm (EHS) mouse sarcoma cells).

Experimental Example 13: Comparison of Gene Expression in Brain Organoid (Gene Ontology)

For the brain organoid cultured in Matrigel® (basement membrane matrix secreted by Engelbreth-Holm-Swarm (EHS) mouse sarcoma cells) and the brain organoid cultured in the dBEM, transcript expression analysis was used to comparatively analyze characteristics of both organoids.

RNA-sequencing was used to compare gene expression patterns between the two groups based on the gene ontology (GO) category analysis.

The genes which had been increased in the dBEM group as compared with the Matrigel® (basement membrane matrix secreted by Engelbreth-Holm-Swarm (EHS) mouse sarcoma cells) group (filtering condition: difference of 1.2 or more, p<0.05, FDR<0.1, n=3) were clustered, and the gene ontology (GO) analysis was performed.

Figure 15A:
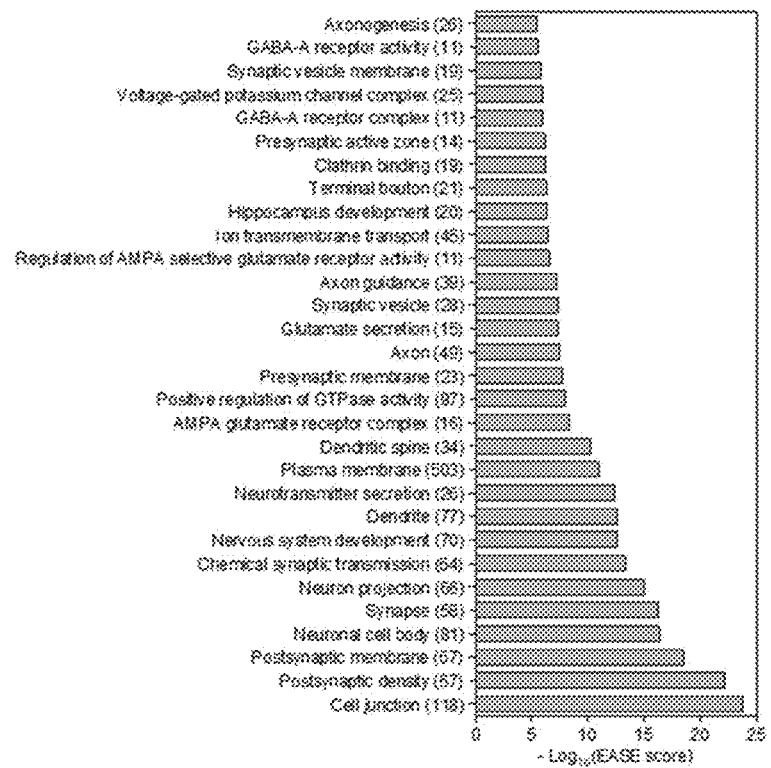

Referring to FIG. 15A, the 30 GO terms with the highest score were mostly associated with the nervous system.

In particular, the brain organoid cultured in the dBEM exhibited increased expression of many markers associated with electrophysiological functions such as synapse and neurotransmitter transmission. These results suggest that the brain organoid is efficiently induced in a case of being cultured in the developed dBEM as compared with a case of being cultured in the existing Matrigel® (basement membrane matrix secreted by Engelbreth-Holm-Swarm (EHS) mouse sarcoma cells) condition.

Referring to FIGS. 15B to 15I, the expression of genes associated with pluripotency was increased, and the expression of forebrain-associated markers and mature neuron-associated markers was also increased.

In particular, glial-associated markers are known to be detected following the expression of neuron-associated markers in the culture of the brain organoid.

The associated markers were increased in the dBEM group, and the results indicate that a degree of maturation of the brain organoid in the dBEM group is promoted. In addition, the expression of many genes associated with ECM interaction and cell adhesion was increased.

Figure 16:
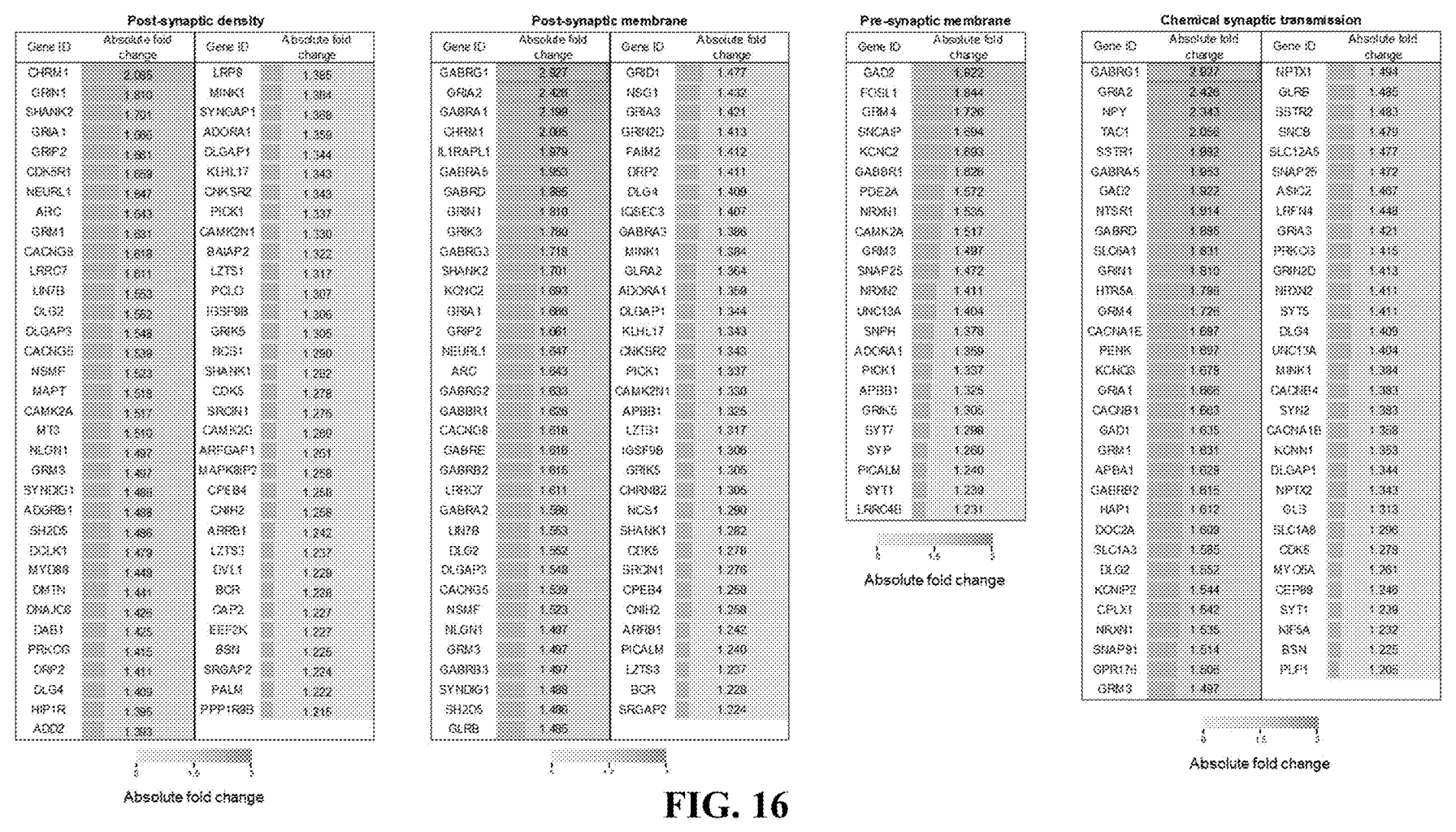

Referring to FIG. 16, the gene ontology (GO) was used to analyze the genes which had been significantly increased (p-value<0.05, FDR<0.1) 1.2-fold or more as compared with the Matrigel® (basement membrane matrix secreted by Engelbreth-Holm-Swarm (EHS) mouse sarcoma cells) group, and as a result, the expression of many genes associated with synaptic chemical signaling was increased.

Figure 17:
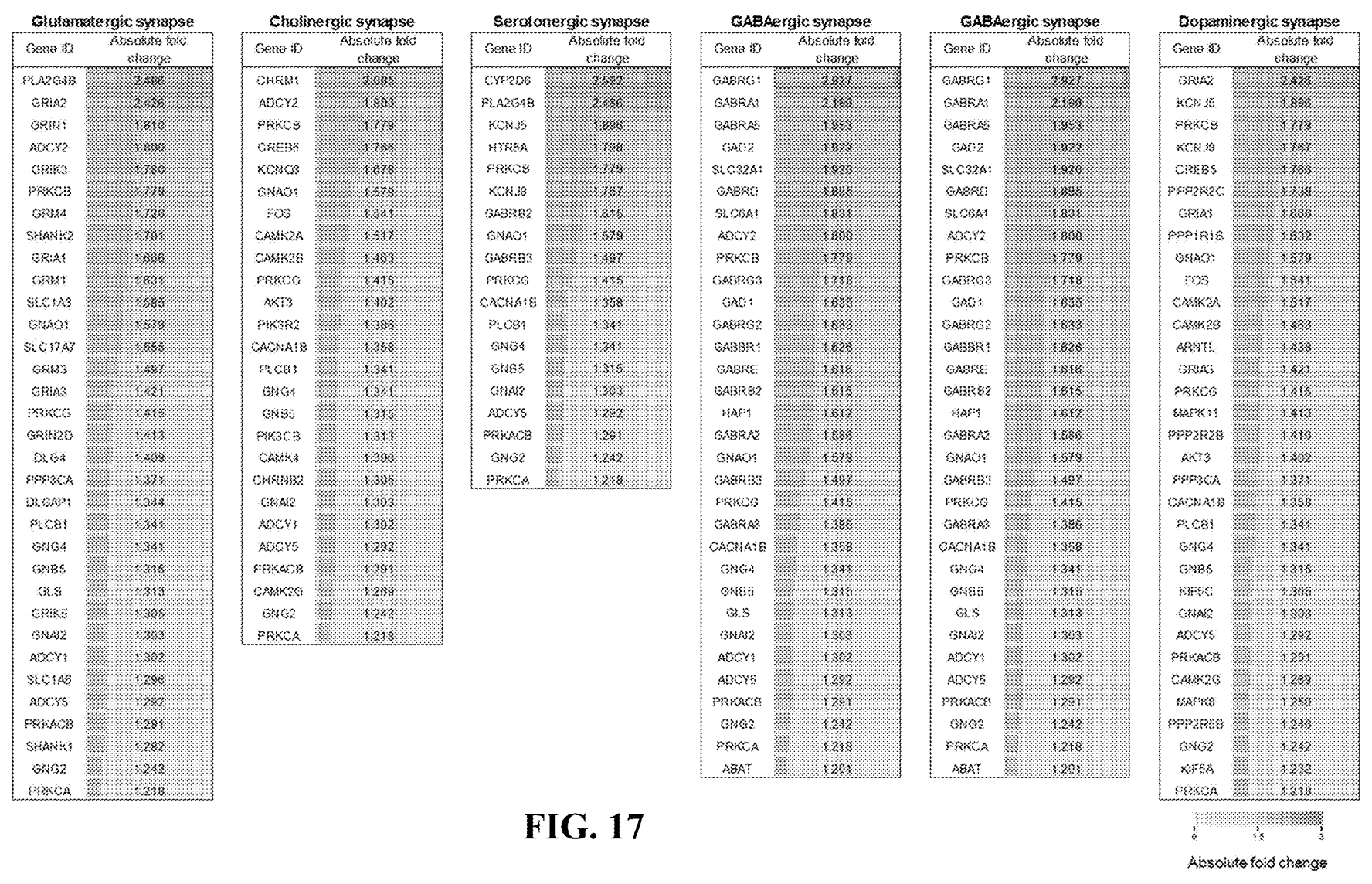

Referring to FIG. 17, the KEG pathway was used to analyze the genes which had been significantly increased (p-value<0.05, FDR<0.1) 1.2-fold or more as compared with the Matrigel® (basement membrane matrix secreted by Engelbreth-Holm-Swarm (EHS) mouse sarcoma cells) group, and as a result, the expression of genes associated with neuron synapses of various subtypes was increased.

The foregoing description of the present invention is for illustrative purposes, and it should be understood by those of ordinary skill in the art that various changes and modifications may be made without departing from the technical spirit or essential features of the present invention. It is therefore to be understood that the above-described embodiments are illustrative in all aspects and not restrictive. For example, each constitutional element described as a single entity may be implemented in a distributed manner. Likewise, constitutional elements described as distributed may also be implemented in a combined form.

The scope of the present invention is defined by the appended claims, and all changes or modifications deduced from the meaning and scope of the claims and their equivalents should be construed as being included within the scope of the present invention.

What is claimed is:

1. A method for preparing a brain organoid, comprising:
   (a) stirring brain tissue for 3 to 24 hours in a decellularizing solution and decellularizing the brain tissue, wherein 98% or more of cells of the brain tissue are removed by the decellularization, and the remaining DNA content is 0.01 to 2.0% of that of the brain tissue before the decellularization;
   (b) drying the decellularized brain tissue and lyophilizing the decellularized brain tissue to obtain a powder; and
   (c) gelating the decellularized brain tissue by mixing the powder with a basement membrane matrix derived from Engelbreth-Holm Swarm (EHS) mouse sarcoma cells to obtain a hydrogel composition, wherein the hydrogel composition contains a decellularized brain extracellular matrix(dBEM) in an amount of 0.01 to 2.0 mg/mL, has a glycosaminoglycan (GAG) content of 8 to 10 μg/mg, and exhibits an elastic modulus at 1 Hz of 110 to 130 Pa;

wherein the hydrogel composition contains Protein components comprising Collagen type I α2, Collagen type IV α2, Collagen type IV α5, Collagen type VI α1, Collagen type VI α2, Collagen type VI α3, Fibronectin type III, Fibrinogen γ chain, Laminin α5, Laminin β1, Laminin γ1, Tenascin R, Keratin 1, Brevican, Neurocan, Versican, Heparan sulfate, Prostaglandin, Apolipoprotein E, Apolipoprotein L2, Apolipoprotein O, Galectin-1 and Albumin;

(d) culturing pluripotent stem cell-derived cells in the hydrogel composition in a three-dimensional culture condition for 45 to 75 days, to obtain a brain organoid exhibiting neural tube formation, wherein expression of neuronal markers selected from Nestin, Tuj1, NeuN, MAP2, Pax6, FoxG1, and Sox2 is confirmed; and (e) confirming differentiation of the brain organoid by (i) identifying of reactivity of the brain organoid to glutamate and gamma amino butyric acid (GABA) neurotransmitter; (ii) identifying expression of N-Cadherin; and (iii) analyzing a development of cortical layer and forebrain.

* * * * *